US011225601B2

(12) United States Patent
Ishow et al.

(10) Patent No.: US 11,225,601 B2
(45) Date of Patent: Jan. 18, 2022

(54) PHOTO-CROSSLINKABLE EMISSIVE MOLECULAR MATERIALS

(71) Applicants: CENTRE NATIONAL DE LA RECHERCHE SCIENTIFIQUE, Paris (FR); COMMISSARIAT A L'ENERGIE ATOMIQUE ET AUX ENERGIES ALTERNATIVES (CEA), Paris (FR); UNIVERSITE DE NANTES, Nantes (FR)

(72) Inventors: Elena Ishow, Nantes (FR); Simon Olivier, Jallais (FR); Tony Maindron, Grenoble (FR); Bernard Geffroy, L'Hay-les-Roses (FR)

(73) Assignees: CENTRE NATIONAL DE LA RECHERCHE SCIENTIFIQUE, Paris (FR); COMMISSARIAT A L'ENERGIE ATOMIQUE ET AUX ENERGIES ALTERNATIVES (CEA), Paris (FR); UNIVERSITE DE NANTES, Nantes (FR)

( * ) Notice: Subject to any disclaimer, the term of this patent is extended or adjusted under 35 U.S.C. 154(b) by 1009 days.

(21) Appl. No.: 15/552,336

(22) PCT Filed: Feb. 23, 2016

(86) PCT No.: PCT/EP2016/053789
§ 371 (c)(1),
(2) Date: Aug. 21, 2017

(87) PCT Pub. No.: WO2016/135151
PCT Pub. Date: Sep. 1, 2016

(65) Prior Publication Data
US 2018/0030342 A1    Feb. 1, 2018

(30) Foreign Application Priority Data
Feb. 23, 2015    (FR) ...................................... 1551540

(51) Int. Cl.
*C09K 11/06* (2006.01)
*C07C 229/60* (2006.01)
(Continued)

(52) U.S. Cl.
CPC ............ *C09K 11/06* (2013.01); *C07C 223/06* (2013.01); *C07C 229/60* (2013.01);
(Continued)

(58) Field of Classification Search
CPC .................. C09K 11/06; C09K 11/025; C09K 2211/1007; C09K 2211/1029;
(Continued)

(56) References Cited

U.S. PATENT DOCUMENTS 9,597,418 B2 * 3/2017 Ishow ................ A61K 31/7048
2008/0124638 A1 5/2008 Hirose et al.
(Continued)

FOREIGN PATENT DOCUMENTS

EP    1 617 493 A2    1/2006
EP    1 729 327 A1    12/2006
(Continued)

OTHER PUBLICATIONS

Elisa Campioli et al: "Enforcing Luminescence at Organic Nanointerfaces: Luminescence Spatial Confinement and Amplification in Molecular-Based Core-Shell Nanoparticles", Small, vol. 9, No. 11, Jun. 10, 2013 (Jun. 10, 2013), DE, pp. 1982-1988, XP055269194, ISSN: 1613-6810, DOI: 10.1002/smll.201202504.
(Continued)

*Primary Examiner* — Matthew E. Hoban
*Assistant Examiner* — Lynne Edmondson
(74) *Attorney, Agent, or Firm* — Nixon & Vanderhye

(57) ABSTRACT

For applications in the fields of organic electronics and photonics, disclosed are fluorescent charge-transfer compounds emitting in the visible spectral range from blue to
(Continued)

red, including a triarylamine moiety, an electron-withdrawing group and at least two photopolymerizable groups. Also disclosed is a method for manufacturing a film-forming and photo-crosslinkable composition including at least one compound of the invention and its use as a precursor of a photocrosslinked emissive layer.

19 Claims, 10 Drawing Sheets

(51) Int. Cl.
*C07C 255/42* (2006.01)
*C07D 305/06* (2006.01)
*C07F 7/18* (2006.01)
*C07C 223/06* (2006.01)
*H01L 51/00* (2006.01)
*H01L 51/50* (2006.01)

(52) U.S. Cl.
CPC .......... *C07C 255/42* (2013.01); *C07D 305/06* (2013.01); *C07F 7/1804* (2013.01); *H01L 51/0035* (2013.01); *C09K 2211/1007* (2013.01); *C09K 2211/1014* (2013.01); *H01L 51/5012* (2013.01)

(58) Field of Classification Search
CPC .... C09K 2211/1014; C09K 2211/1018; C07C 255/42; C07C 223/06; C07C 229/60; C07D 305/06
USPC .................................................. 252/301.16
See application file for complete search history.

(56) References Cited

U.S. PATENT DOCUMENTS

2010/0308754 A1* 12/2010 Gough ................. H01L 51/004
  315/363
2015/0329772 A1   11/2015 Heil et al.

FOREIGN PATENT DOCUMENTS

| WO | 01/08230 A1 | 2/2001 |
| WO | 2009/061314 A1 | 5/2009 |
| WO | 2014/106522 A1 | 7/2014 |

OTHER PUBLICATIONS

H. Shirakawa et al.: "Synthesis of Electrically Conducting Organic Polymers : Halogen Derivatives of Polyacetylene, (CH),", (Department of Chemistry and Department of Physics, Laboratory for Research on the Structure of Matter, University of Pennsylvania, Philadelphia 19104), Satisfactory microanalytical data were obtained for this compound, J.C.S. Chem. Comm., 1977, pp. 579-580.
Du et al.: "Cross-linked Alq3—containing polymers with improved electroluminescence efficiency used for OLED", Macromol. Rapid. Commun., vol. 27, Jan. 2006 (Jan. 1, 2006), pp. 412-417.
Zuniga et al.: "Approaches to solution-processed multilayer organic light-emitting diodes based on cross-linking", Chem. Mater., vol. 23, No. 3, Nov. 2011 (Nov. 1, 2011), pp. 658-681.
Biwu Ma et al.: "Multifunctional crosslinkable iridium complexes as hole-transporting/electron blocking and emitting materials for solution-processed multilayer organic light-emitting diodes", Adv. Funct. Mater., vol. 19, 2009, pp. 1024-1031.
Elena Ishow et al., "Multicolor Emission of Small Molecule-Based Amorphous Thin Films and Nanoparticles with a Single Excitation Wavelength" Chem. Mater., vol. 20, 2008, pp. 6597-6599.
International Search Report, dated May 9, 2016, from corresponding PCT/EP2016/053789 application.

* cited by examiner

PHOTO-CROSSLINKABLE EMISSIVE MOLECULAR MATERIALS

FIELD OF THE INVENTION

The present invention relates to the field of organic electronics and photonics. More particularly, this invention relates to fluorescent charge-transfer compounds emitting in the visible spectral range from blue to red, comprising a triarylamine moiety, an electron-withdrawing group and at least two photopolymerizable groups. This invention also relates to a method for manufacturing a film-forming and photo-crosslinkable composition comprising at least one compound of the invention and its use as a precursor of a photocrosslinked emissive layer.

PRIOR ART

The discovery in 1977 by A. J. Heeger, A. G. McDiarmid and H. Shirakawa of π-conjugated polymers, with semiconductor properties, opened the road to a new field for investigation: organic electronics, also called plastic electronics.

Thanks to this new technology, it has become possible to design electronic components using organic molecules as a replacement for silicon.

This change gave rise to increasing interest from the scientific community and from industrialists due to the considerable advantages afforded by the use of organic molecules with regard to that of silicon. For example, organic materials can be applied in very thin layers of hardly a few tens of nanometers on various substrates, in particular via vacuum evaporation techniques, spin coating or inkjet printing to mention only a few; they can be adapted easily to surfaces with a highly varied surface and geometry, which makes it possible to generate flexible and light devices.

Among the various possible application of organic electronics, the development of organic light-emitting diodes (OLEDs) has experienced strong growth in the last few years.

OLEDs are devices constituted of a multilayer of organic and inorganic materials, sandwiched between two electrodes, having as the simplest architecture:
- a transparent substrate (the support material for the diode);
- a transparent anode that generates the holes (i.e. the lack of electrons);
- a cathode, usually metallic, that generates electrons;
- the superposition of several organic layers located between the anode and the cathode comprising at least one electron-transporting layer, a hole-transporting layer and an emissive layer.

By applying a voltage between the two electrodes, with the anode and the cathode generating respectively holes and electrons. These charges migrate to the emissive layer then are recombined by emitting a photon, i.e. light of which the power, and therefore the color, depend on the nature of the emissive material.

The greatest difficulty in manufacturing OLEDs resides in the multilayer deposition of the organic materials in such a way that the lower layer is not dissolved during the deposition of the upper layer.

This deposition step is implemented primarily according to two methods: (a) solution process also called wet deposition and (b) vapor deposition.

The solution process method (a) is a method that is easily implementable, inexpensive and extendable to large-area substrates. This deposition method is mostly used when the organic molecules to be deposited are polymers or oligomers. Indeed, polymers or oligomers exhibit good morphological stability (absence of recrystallization) and low molecular diffusion compared to small organic molecules used the same conditions. However, the choice of the solvents used to dissolve the oligomers or polymers before their deposition is delicate. Indeed, in this method, fabricating stacked layers requires successive deposition of several polymer materials on the substrate, each deposition step requiring distinct solvents. As such, the deposition of a second layer using a polymer solution can result in partly dissolving the previously deposited layer. The solution-based deposition method therefore requires the use of "orthogonal" solvents, i.e. solvents that do not dissolve the previously deposited layers. This method also faces issues related to the ejection of solutions from printing nozzles or the formation of satellite droplets when using inkjet deposition technique, highly dependent on the polymer molecular weight and the viscosity of the polymer solutions.

Solutions of low-molecular-weight molecules can be injected more easily, thereby making solution-based process very attractive. However, the use of small molecules most often results in intermolecular aggregation phenomena responsible for the degradation in the material optical qualities and performances in emission and electroluminescence.

The vapor deposition method (b) represents until now, the method of choice for depositing small organic molecules. This method has the advantage of providing multilayered structures that are perfectly controlled, and consists in evaporating low-molecular-weight molecules on a substrate. Vapor deposition does not require the use of solvent. However, contrary to solution process, the deposition rate is limited and protecting substrate areas from material deposition using a mask is mandatory. Moreover, the need of several evaporators connected in series to ensure continuous vacuum makes this technique more burdensome, in particular when cleaning evaporation chain is required. Finally, material spitting can occur resulting in surface irregularities, and thus short-circuits. Carrying out vapor deposition on substrates of large surface area is moreover delicate due to the limited-size evaporators, which results in prohibitive manufacturing costs.

Consequently, there is a need to provide a solution-based deposition method for small organic molecules that can provide insoluble emissive layers in a more handy and cost-effective manner in regards to the later deposition technique.

In particular, there is a need to develop small molecules that can be adapted to solution-based deposition method implementable for the fabrication of multilayered architectures 1) without altering each layer successively deposited and 2) allowing for easier production of large-area substrate. Work in the field of hole-transporting layers has already been carried out and provided high-performance results. On the other hand, very little attention has been given to the deposition of emissive layers, namely layers deposited on hole-transporting layers and preceding electron-transporting layers (or hole blocking layers).

The optimization of the deposition conditions strongly depends on the structure of the organic molecules constituting the organic emissive layer (emissive molecules).

It is therefore necessary to provide organic molecules that can form an organic emissive layer in a controlled manner; in particular in order to obtain a multilayered electronic or photonic device. These organic molecules must in particular make optimization of the deposition method possible, i.e.

reducing the manufacturing costs and wastes while still maintaining a high level of performance.

Surprisingly, the Applicant was able to elaborate small molecule-based compounds which, after deposition and photopolymerization, form layers of high-surface qualit, and emitting in the solid state. These compounds are triarylamine derivatives comprising photopolymerizable groups and an electron-withdrawing group, giving rise to materials with high-film forming (filmogenicity) and emissive properties. They can easily be deposited in solution, making the method easily transferrable to large-area substrates. In addition, they allow for the fabrication of emissive layers that are uniform, insoluble and stable over time after photo-crosslinking in gentle conditions.

The triarylamine derivatives have received very little attention as photopolymerizable emissive molecules and/or as precursors of emissive organic layers.

Until now, mostly symmetrical triarylamine derivatives have been used primarily in organic electronics as hole-transporting layer components but have never been developed as precursors of emissive layers.

For example, Kido et al. (EP 1 617 493) described the preparation of a layer containing a charge-transfer complex comprising a hole-transporting compound based on a triarylamine moiety.

Baldo et al. (EP 1 729 327) developed organic light-emitting diodes wherein iridium or osmium complexes with a triarylamine unit are used as hole-transporting layers.

Hirose et al. (US 2008/0124638) and Gough et al. (WO 2009/061314) reported a method for manufacturing an electronic device comprising a hole-transporting layer constituted of triarylamine derivatives having photopolymerizable functions.

Contrary to the precursor compounds of emissive layers, the hole-transporting layers have a chemical structure that does not comprise electron-withdrawing groups, hence they do not intrinsically emit light in the visible range. Indeed, hole-transporting layers are primarily constituted of electron-rich compounds, easily oxidizable in order to facilitate internal hole migration.

On the other hand, emissive layers are organic layers capable of transporting both electrons and electronic holes so that both charges recombine as an exciton inside the emissive layers, and allow in fine for photon emission.

Until now, the development of emissive molecules primarily concerns organometallic complexes such as tris-(8-hydroxyquinoline) aluminum ($Alq_3$) or coordination complexes like iridium complexes comprising photopolymerizable groups (Du et al., "Cross-linked $Alq_3$-containing polymers with improved electroluminescence efficiency used for OLED", *Macromol. Rapid. Commun.*, Vol. 27, January 2006, pp 412-417; Ma et al., "Multifunctional crosslinkable iridium complexes as hole-transporting/electron blocking and emitting materials for solution-processed multilayer organic light-emitting diodes", Adv. Funct. Mater. Vol. 19, 2009, pp 1024-1031; Zuniga et al., "Approaches to solution-processed multilayer organic light-emitting diodes based on cross-linking", *Chem. Mater.*, Vol. 23, N° 3, November 2011, pp 658-681). However, polymerization and/or crosslinking of these organometallic/coordination complexes require high reaction temperatures and annealing steps that can alter the performance of the obtained emissive layers. Consequently, it is necessary to develop organic emissive molecules that can be polymerized in gentle conditions.

In addition, emissive layers mostly operate by adding an emissive dopant (Forrest et al. (WO 01/08230)). However, doping an organic emissive layer for manufacturing purpose generally results in aggregation issues due to molecular reorganization or diffusion of organic molecules within the layer. It is therefore necessary to develop precursors of organic emissive layers for getting rid of dopant.

Definitions

In this invention, the terms herein below are defined as follows:

"About": preceding a figure means plus or minus 10% of the value of said figure;

"Alkene": relates to a branched or linear unsaturated hydrocarbon chain, comprising at least 2 carbon atoms, characterized by the presence of at least one double covalent bond between two carbon atoms;

"Alkyne": relates to a branched or linear unsaturated hydrocarbon chain, comprising at least 2 carbon atoms, characterized by the presence of at least one triple covalent bond between two carbon atoms;

"Alkyl": relates to an optionally substituted, branched or linear hydrocarbon chain, comprising from 1 to 20 carbon atoms; preferably, the term alkyl including the alkyl chains comprising from 1 to 10 carbon atoms; preferably, methyl, ethyl, propyl, isopropyl, n-butyl, sec-butyl, isobutyl, tert-butyl, pentyl, hexyl, heptyl, octyl, nonyl, decyl;

"Alkylacryloyl": relates to a $CH_2$=CR—CO— group wherein R represents an alkyl group; preferably, a methyl group;

"Alkyloxetane": relates to an oxetane group substituted with at least one alkyl group;

"Allyl": relates to the polymerizable group —$CH_2$—CH=$CH_2$;

"Amorphous": refers to a material wherein the atoms or the molecules do not have a medium or large distance, which distinguishes them from crystalline materials;

"Aryl": relates to a mono- or polycyclic system of 5 to 32 atoms; preferably, from 6 to 14 atoms; more preferably, from 6 to 10 carbon atoms having one or several aromatic rings. According to the invention, the aryl group is preferentially a phenyl group;

"Acryloyl": relates to a $CH_2$=CH—CO— group;

"Acrylamide": relates to a $CH_2$=CH—CO—NH— group;

"Carboxy": relates to a —COOH group;

"Chiral center": refers to a carbon linked to four different atoms or groups of atoms;

"Cinnamate": refers to a —OCOCH=CH—$C_6H_5$ group;

"Cyanovinylidene": relates to a —CH=C(CN)— group;

"Dicyanovinylidene": relates to a —CH=C(CN)$_2$ group;

"Doping": refers to a chemical method consisting in introducing into the matrix of a semiconductor material, atoms or molecules in order to increase either the number of electrons (n-type doping) or the number of "holes" (p-type doping) in said material; these dopings make it possible to modify the conduction and/or emission properties of the material involved;

"Electron-withdrawing": refers to an atom or functional group that has electronegativity greater than that of the hydrogen atom and therefore having the capability to attract electrons within the bond; in particular, to an atom or a group which is electron-withdrawing by negative mesomeric or inductive effects, selected from halogens (—F, —Br or —I), cyano (—CN), carboxyl (—COOH), ester (—COOR wherein R represents a alkyl, alkene, alkyne or aryl group), quaternary ammonium (—$NH_3^+$ or —$NR_3^+$), sulfonium (—$SR_2^+$), sulfoxy (—SOR), sulfone (—$SO_2R$), diarylammonium ($Ar_2NH^+$), pyridinium ($C_5H_6N^+$), aldehyde (—CHO), oxo (—CO—), benzothiadiazole; preferably selected from halogens (—F, —Br or —I), cyano (—CN), carboxyl (—COOH), ester (—COOR wherein R represents a alkyl, alkene or alkyne group), quaternary ammonium (—$NH_3^+$ or —$NR_3^+$), diarylammonium ($Ar_2NH^+$), pyridinium ($C_5H_6N^+$), aldehyde (—CHO), oxo (—CO—), benzothiadiazole. In terms of this invention, an electron-withdrawing group may include one or several electron-withdrawing mesomeric or negative inductive groups;

"Emissive": refers to a chemical entity able to emit a photon with energy in the visible range;

"Heteroaryl": relates to an aryl group having at least one atom different from an carbon or hydrogen atom; preferably, said atom being selected from N, S, P or O;

"Oxetane": relates to a heterocyclic group of formula $C_3H_6O$ which consists in a cyclic ether having four atoms: three carbon and one oxygen;

"Oxo": relates to a C=O group;

"Photoinitiator": refers to a compound able to initiate a polymerization reaction following light irradiation at a certain wavelength; in particular, in the UV— visible— near infrared range;

"Photopolymerizable": refers to a compound capable of polymerizing following a reaction photoinduced by illuminating a photoinitiator at a certain wavelength; in particular, in the UV— visible—near infrared range;

"Photo-crosslinkable": refers to a compound comprising at least two polymerizable chemical functions allowing for the formation of a network of chemical bonds, and of which the initiation of the polymerization in solid phase is induced by the irradiation of a photoinitiator at a certain wavelength;

"Styryl": relates to a polymerizable group of formula —$C_6H_4$—CH=$CH_2$.

DETAILED DESCRIPTION

Compounds

This invention relates to a photopolymerizable emissive compound of general formula (I):

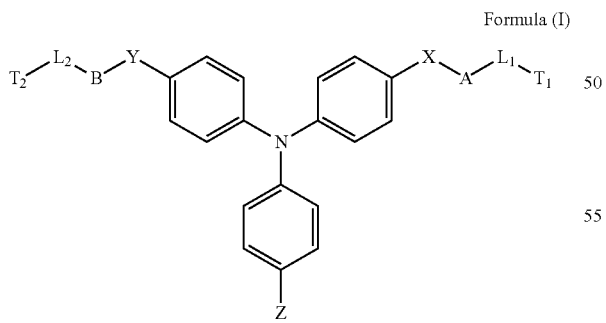

Formula (I)

wherein X and Y each independently represent an aryl or heteroaryl; preferably, a phenyl group;

A and B each independently represent a chiral center; preferably, A and B simultaneously represent a —CHMe— group;

$L_1$ and $L_2$ each independently represent an alkyl group comprising 1 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; preferably, $L_1$ and $L_2$ each independently represent an alkyl group comprising 3 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; more preferably, $L_1$ and $L_2$ simultaneously represent an alkyl chain interrupted by at least one oxygen atom and substituted with at least one oxo group;

$T_1$ and $T_2$ each independently represent a photopolymerizable group selected from at least one acryloyl, alkylacryloyl, oxetane, alkyloxetane, styryl, allyl, acrylamide, methacrylamide or cinnamate; preferably, $T_1$ and $T_2$ simultaneously represent an acryloyl group or an alkyloxetane group;

Z represents an electron-withdrawing group; preferably, Z represents an aldehyde, dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

According to one embodiment, the electron-withdrawing group Z is the group 4-phenylbenzo[c][1,2,5]thiadiazolyl:

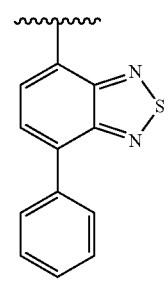 [SMILES: *c1ccc(-c2ccccc2)c2nsnc12]

In one embodiment, the preferred compounds of general formula (I) are those of formula

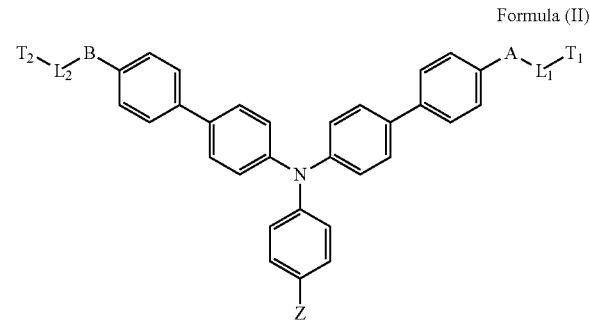

Formula (II)

wherein A and B each independently represent a chiral center, preferably A and B simultaneously represent a —CHMe— group;

$L_1$ and $L_2$ each independently represent an alkyl group comprising 1 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; preferably, $L_1$ and $L_2$ each independently represent an alkyl group comprising 3 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; more preferably, $L_1$ and $L_2$ simultaneously represent an alkyl chain interrupted by at least one oxygen atom and substituted with at least one oxo group;

$T_1$ and $T_2$ each independently represent a photopolymerizable group selected from at least one acryloyl, alkylacryloyl, oxetane, alkyloxetane, styryl, allyl, acrylamide, methacrylamide or cinnamate; preferably, $T_1$ and $T_2$ simultaneously represent an acryloyl group or an alkyloxetane group; and Z represents an electron-withdrawing group; preferably, an aldehyde, dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

According to one embodiment, the preferred compounds of general formula (II) are those described in the following table:

| Compound No. | A = B | $L_1 = L_2$ | $T_1 = T_2$ | Z |
|---|---|---|---|---|
| II-a | —CHMe— | | | |
| II-b | —CHMe— | | | |
| II-c | —CHMe— | | | |
| II-d | —CHMe— | | | |
| II-e | —CHMe— | | | |
| II-f | —CHMe— | | | |
| II-g | —CHMe— | | | |
| II-h | —CHMe— | | | |

-continued

| Compound No. | A = B | L₁ = L₂ | T₁ = T₂ | Z |
|---|---|---|---|---|
| II-i | —CHEt | succinate diester linker | acrylate | dicyanovinyl |
| II-j | —CHEt | succinate diester linker | ethyl-oxetane | dicyanovinyl |
| II-k | —CHEt | succinate diester linker | acrylate | aldehyde |
| II-l | —CHEt | succinate diester linker | ethyl-oxetane | aldehyde |
| II-m | —CHEt | succinate diester linker | acrylate | carboxylic acid |
| II-n | —CHEt | succinate diester linker | ethyl-oxetane | carboxylic acid |
| II-o | —CHMe | succinate diester linker | acrylamide | dicyanovinyl |
| II-p | —CHMe | succinate diester linker | acrylamide | aldehyde |
| II-q | —CHMe | succinate diester linker | acrylamide | carboxylic acid |
| II-r | —CHEt | succinate diester linker | acrylamide | dicyanovinyl |

| Compound No. | A = B | L₁ = L₂ | T₁ = T₂ | Z |
|---|---|---|---|---|
| II-s | —CHEt | ⸜O-C(O)-CH₂CH₂-C(O)-O-CH₂CH₂⸝ | ⸜CH=CH-C(O)-N⸝ | ⸜CHO |
| II-t | —CHEt | ⸜O-C(O)-CH₂CH₂-C(O)-O-CH₂CH₂⸝ | ⸜CH=CH-C(O)-N⸝ | ⸜C(O)OH |
According to one embodiment, the preferred compound of general formula (II) is bis(2-(acryloyloxy)ethyl) O,O'-(((((4-(2,2-dicyanovinyl)phenyl)azanediyl)bis([1,1'-biphenyl]-4',4-diyl))bis(ethane-1,1-diyl)) disuccinate of formula (II-a):
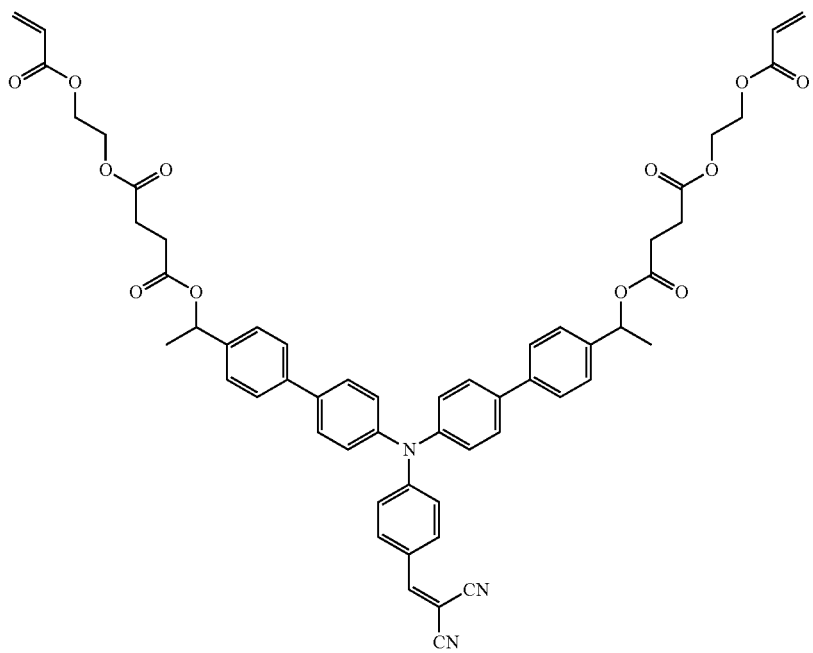
Formula (II-a)

According to one embodiment, the preferred compound of general formula (II) is the compound O,O'-((((4-(2,2-dicyanovinyl)phenyl)azanediyl)bis([1,1'-biphenyl]-4',4-diyl))bis(ethane-1,1-diyl)) bis((3-ethyloxetan-3-yl)methyl) disuccinate of formula (II-b):

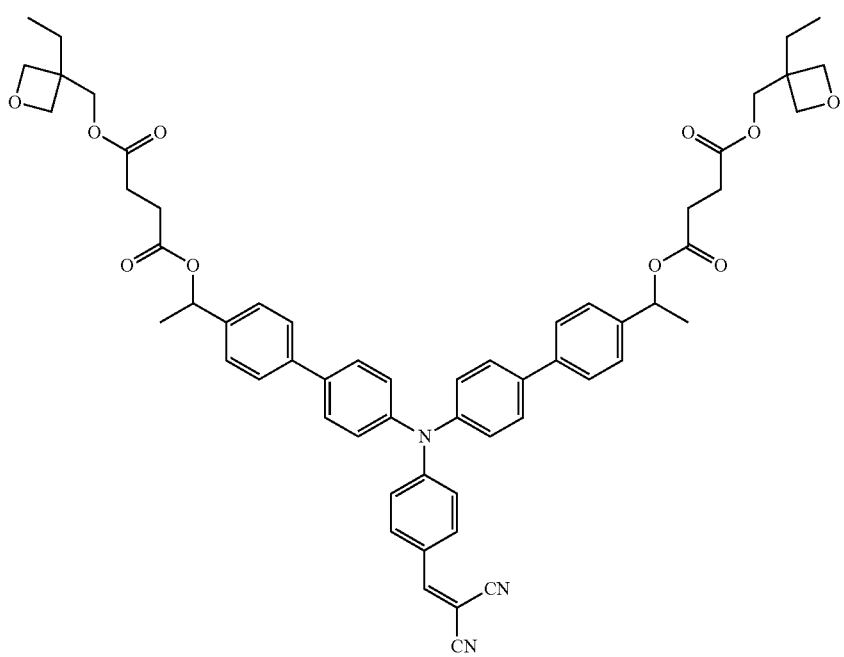

Formula (II-b)

According to one embodiment, the compound of the invention is a photo-crosslinkable emissive compound of general formula (II-a), (II-b), (II-c) or (II-d).

According to one embodiment, the compound of the invention is amorphous for temperatures ranging from −20° C. to 200° C.; preferably, for temperatures ranging from −10° C. to 100° C.; more preferably, for temperatures ranging from 0° C. to 30° C.

According to one embodiment, the compound of the invention has a glass transition temperature ($T_g$) less than or equal to 30° C.; preferably, less than 30° C.; more preferably, less than 20° C. According to one embodiment, the compound of the invention has a glass transition temperature ($T_g$) equal to about 28° C. According to one embodiment, the compound of the invention has a glass transition temperature ($T_g$) equal to about 12° C.

According to one embodiment, the compound of the invention comprises at least one chiral center giving rise to a racemic mixture of stereoisomers.

In one embodiment, the compound of the invention is a solid-state emissive molecule. According to one embodiment, the compound of the invention displays an emission spectrum that is function of the chemical structure of its electron-withdrawing group Z. According to one embodiment, the compound of the invention emits in the visible range. According to one embodiment, the compound of the invention emits in the red, the green or the blue of the white light spectrum. According to a one embodiment, the compound of the invention emits in the red. According to one embodiment, the compound of the invention emits in the green. According to one embodiment, the compound of the invention emits in the blue.

Intermediate Compounds

This present invention also relates to the intermediate compounds obtained during the method for manufacturing compounds of formula (I). In particular, the invention relates to an intermediate compound of general formula:

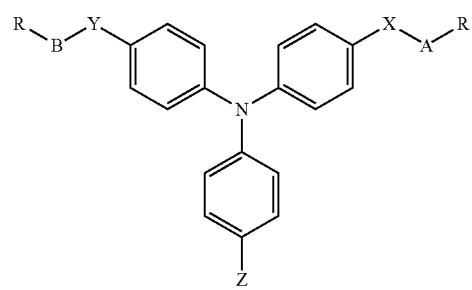

wherein X and Y each independently represent an aryl or heteroaryl; preferably, phenyl group;

R represents a —OH or —OTBDMS group;

A and B each independently represent a chiral center; preferably, A and B simultaneously represent a —CHMe— group; and Z represents an electron-withdrawing group; preferably, Z represents an aldehyde, dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

Composition

The invention also relates to a composition comprising the compounds of the invention. In particular, the invention relates to a composition comprising at least one compound of general formula (I):

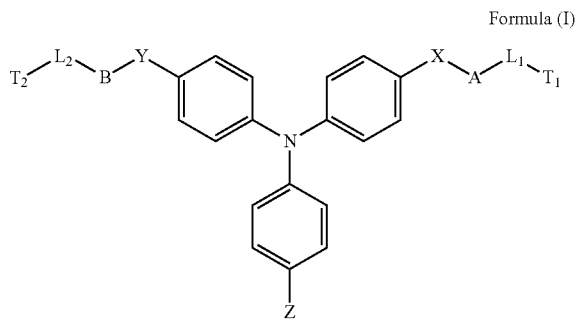

Formula (I)

wherein A, B, X, Y, $L_1$, $L_2$, $T_1$, $T_2$ and Z are defined as herein above.

In one embodiment, the composition comprises at least one compound of general formula (II):

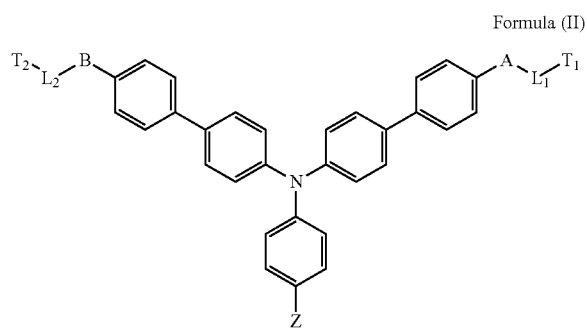

Formula (II)

wherein A, B, $L_1$, $L_2$, $T_1$, $T_2$ and Z are defined as herein above.

In one embodiment, the composition comprises at least one compound of formula (I) and/or (II), an initiator and an organic solvent.

In one embodiment, the composition comprises at least one compound of formula (I) and/or (II), a photoinitiator and an organic solvent.

According to one embodiment, said composition allows for the fabrication of an amorphous thin film of photo-crosslinkable monomers without any detectable micro-aggregate. In one embodiment, said composition allows obtaining a photo-crosslinkable film of the compounds of the invention.

In one embodiment, the composition comprises the mixture of at least two different compounds of formula (I). Without willing to be bound by any theory, the Applicant observes that the structural similarity of the compounds in said composition allows for limited segregation phenomena and makes possible the simultaneous photopolymerization of the various compounds of the invention by using a single irradiation wavelength.

According to one embodiment, the composition comprises the mixture of at least one compound of general formula (I) and of at least one compound of general formula (II).

According to one embodiment, the composition comprises the mixture of at least two compounds of general formula (II). According to one embodiment, the composition comprises the mixture of at least three compounds of general formula (II).

According to one embodiment, the composition comprises the mixture of at least two compounds of general formula (I) and/or of general formula (II), wherein said compounds have separate emission spectra. According to one embodiment, the composition comprises the mixture of at least two compounds of general formula (I) and/or of general formula (II), wherein said compounds emit in the red, green and/or blue.

According to one embodiment, the concentration of the compounds of the invention in the composition ranges from $10^{-3}$ to 1 mol/L; preferably, from $10^{-2}$ to 0.1 mol/L; more preferably, is about $1 \cdot 5 \cdot 10^{-2}$ mol/L.

According to one embodiment, the compounds of the invention in the composition are at a weight concentration ranging from 1 to 100 g/L; preferably, from 10 to 50 g/L; more preferably, being about 15 g/L.

According to one embodiment, said composition further comprises an organic solvent such as but not limited to hydrocarbons, such as cyclohexane or methylcyclohexane, petroleum ether, toluene or xylene; chlorinated hydrocarbons, such as 1,2-dichloroethane, trifluoromethylbenzene, chloroform or dichloromethane; hydroxyls, such as methanol, ethanol, isopropanol, n-propanol or n-butanol; ethers, such as diethyl ether, diisopropyl ether, 2-methyltetrahydrofuran or dioxane; ketones, such as acetone or butanone; amides, such as acetamide, dimethylacetamide, N-methylpyrrolidone (NMP) or dimethylformamide (DMF); nitriles, such as acetonitrile; carboxylic acids, such as formic acid or acetic acid; esters, such as ethyl acetate, alone or in a mixture, propylene carbonate.

According to one embodiment, the solvent is polar. According to one embodiment, the solvent is apolar. According to one embodiment, the solvent is a green solvent.

According to one preferred embodiment, the solvent is chloroform or toluene.

According to one embodiment, the photoinitiator is selected from 2-tert-butylanthraquinone, camphorquinone, diphenyl(2,4,6-trimethylbenzoyl)phosphine oxide, 9,10-phenanthrenequinone, phenylbis(2,4,6-trimethylbenzoyl) phosphine oxide, 2-benzyl-2-(dimethylamino)-4'-morpholinobutyrophenone, 3,6-bis(2-methyl-2-morpholinopropionyl)-9-octylcarbazole, 4'-tert-butyl-2',6'-dimethylacetophenone, 2,2-diethoxyacetophenone, 4'-ethoxyacetophenone, 3'-hydroxyacetophenone, 4'-hydroxyacetophenone, 1-hydroxycyclohexylphenylcetone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, benzoin, benzoinethyl ether, benzoinmethyl ether, 4,4'-dimethylbenzoin, 4,4'-dimethylbenzile, benzophenone, benzoyl biphenyl, 4,4'-bis(diethylamino)benzophenone, 4,4'-dihydroxybenzophenone, 3,4-dimethylbenzophenone, 3-hydroxybenzophenone, 4-hydroxybenzophenone, 2-methylbenzophenone, 3-methylbenzophenone, 4-methylbenzophenone, methyl benzoylformate, Michler's ketone, 1-chloro-4-propoxy-9H-thioxanthen-9-one, 2-chlorothioxanthen-9-one, 2,4-diethyl-9H-thioxanthen-9-one, isopropyl-9H-thioxanthen-9-one, 10-methylphenothiazine, thioxanthen-9-one, diaryliodonium hexafluorophosphate salt, diaryliodonium hexafluoroantimonate salt, triarylsulfonium hexafluorophosphate salt, hexafluorophosphate, triarylsulfonium hexafluoroantimonate salt.

According to one preferred embodiment, the photoinitiator is diphenyl(2,4,6-trimethylbenzoyl)phosphine oxide.

According to one embodiment, the photoinitiator in the composition is at a molar concentration ranging from $1 \cdot 10^{-4}$ to $5 \cdot 10^{-3}$ mol/L; preferably, less than $1 \cdot 10^{-3}$ mol/L; more preferably, about $7 \cdot 7 \cdot 10^{-4}$ mol/L.

According to one embodiment, the photoinitiator in the composition is at a weight concentration ranging from 0.1 to 1 g/L; preferably, less than 0.5 g/L; more preferably, about 0.27 g/L. According to one preferred embodiment, the ratio of the molar concentration of the photoinitiator with the molar concentration in compounds of general formula (I) and/or (II) ranges from 0.01 to 1; preferably, this ratio is equal to about 0.02.

According to one embodiment, the composition is kept away from light.

According to one embodiment, the composition is stored at low temperatures (refrigerator or freezer).

According to one embodiment, the composition is stored in an inert atmosphere.

Nanoparticles

The invention also relates to a fluorescent organic nanoparticle comprising at least one compound of general formula (I):

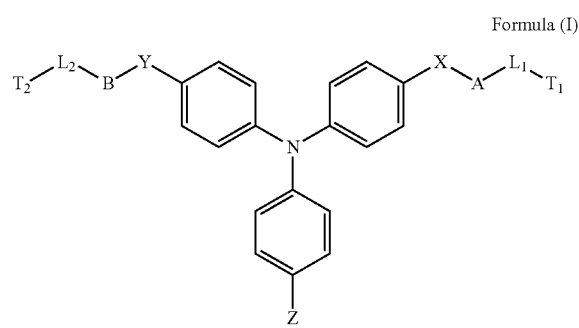

Formula (I)

wherein A, B, $L_1$, $L_2$, $T_1$, $T_2$, X, Y and Z are defined as hereinabove.

According to one embodiment, the fluorescent nanoparticle is constituted of compounds of general formula (I).

According to one embodiment, the fluorescent nanoparticle is a photocrosslinked fluorescent nanoparticle.

According to one embodiment, the fluorescent nanoparticle is insoluble.

According to one embodiment, the fluorescent nanoparticle comprises compound of formula (II-a). According to one embodiment, the fluorescent nanoparticle comprises compound of formula (II-b). According to one embodiment, the fluorescent nanoparticle comprises compound of formula (II-c).

According to one embodiment, the fluorescent nanoparticle comprises a mixture of compounds of formula (II-a), (II-b) and/or (II-c). In one embodiment, the fluorescent nanoparticle comprises a mixture of compounds (II-a) and (II-c). In one embodiment, the fluorescent nanoparticle comprises a mixture of compounds (II-a) and (II-b). In one embodiment, the fluorescent nanoparticle comprises a mixture of compounds (II-b) and (II-c).

According to one embodiment, the nanoparticle of the invention is an emissive nanoparticle. According to one embodiment, the nanoparticle of the invention emits in the visible range. According to one embodiment, the nanoparticle of the invention emits in the red, the green or the blue of the white light spectrum. According to a one embodiment, the nanoparticle of the invention emits in the red. According to one embodiment, the nanoparticle of the invention emits in the green. According to one embodiment, the nanoparticle of the invention emits in the blue.

According to one embodiment, the fluorescent nanoparticle has a diameter less than 300 nm; preferably less than 200 nm; more preferably, less than 100 nm.

Kit

The invention also relates to a kit comprising a first compartment comprising at least one compound of formula (I) and/or (II) and an organic solvent, and a second compartment comprising the photoinitiator.

In one embodiment, the second compartment further comprises a solvent; preferably, an organic solvent; more preferably, a volatile organic solvent.

Method for Manufacturing Compounds

The invention also relates to a method for manufacturing a compound of general formula (I):

wherein A, B, $L_1$, $L_2$, $T_1$, $T_2$, X, Y and Z are defined as hereinabove, comprising:

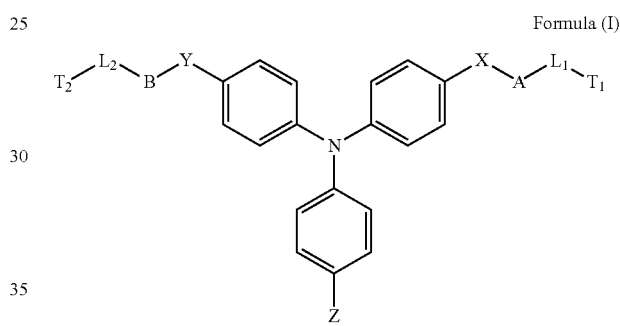

Formula (I)

(i) the synthesis of the intermediate compound of general formula (III-2):

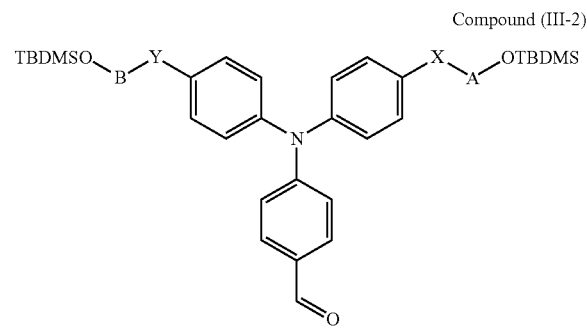

Compound (III-2)

wherein A, B, X and Y are defined as hereinabove, obtained by the reaction of the 4-di(4-bromophenyl)aminobenzaldehyde with the compound of formula (III-1):

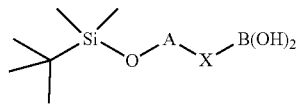

also noted as

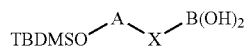

wherein A represents a chiral center; preferably, A represents a —CHMe— group; and X represents an aryl or heteroaryl; preferably, a phenyl group;

(ii) a deprotection reaction;

(iii) optionally, a step of modifying the aldehyde group into another electron-withdrawing group Z' allowing the provision of intermediate compound of formula (III-3bis):

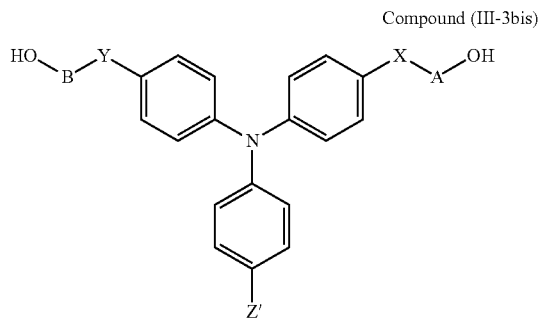

Compound (III-3bis)

wherein A, B, X and Y are defined as hereinabove and Z' represents an electron-withdrawing group; preferably, Z' is a dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate;

(iv) and, comprising a step of modifying the compound obtained in (ii) or in (iii) allowing for the introduction of spacers L comprising at least one photopolymerizable group T.

According to one embodiment, the preferred compound of formula (III-1) is 4{1-[(tert-butyldimethylsilyl)oxy]ethyl}phenyl boronic acid:

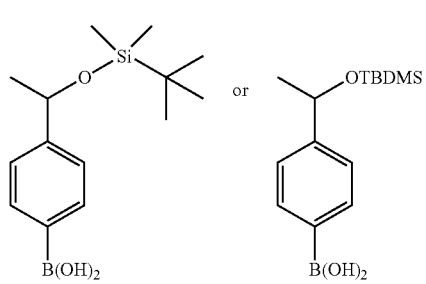 [SMILES: CC(O[Si](C)(C)C(C)(C)C)c1ccc(B(O)O)cc1 ; CC(O[Si](C)(C)C(C)(C)C)c1ccc(B(O)O)cc1]

According to one embodiment, the preferred compounds of formula (III-2) are the compounds of general formula (III'-2):

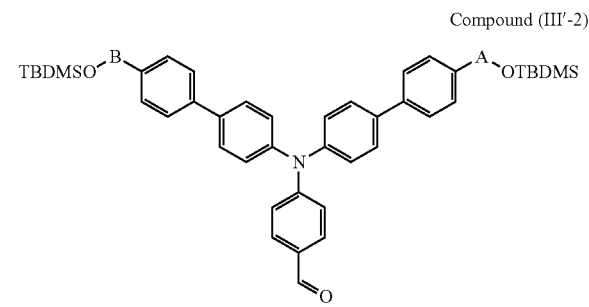

Compound (III'-2)

According to one embodiment, the preferred compound of formula (III'-2) is 4-(bis(4'-(1-((tert-butyldimethylsilyl)oxy)ethyl)-[1,1'-biphenyl]-4-yl)amino)benzaldehyde:

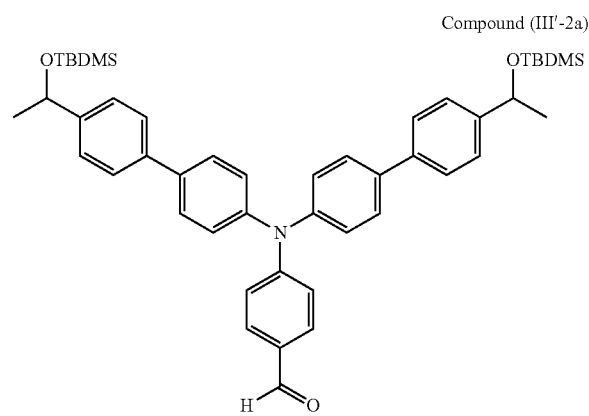 [SMILES: CC(O[Si](C)(C)C(C)(C)C)c1ccc(-c2ccc(N(c3ccc(C=O)cc3)c3ccc(-c4ccc(C(C)O[Si](C)(C)C(C)(C)C)cc4)cc3)cc2)cc1]

Compound (III'-2a)

According to one embodiment, the compound of formula (III-3) are the compounds of general formula (III'-3):

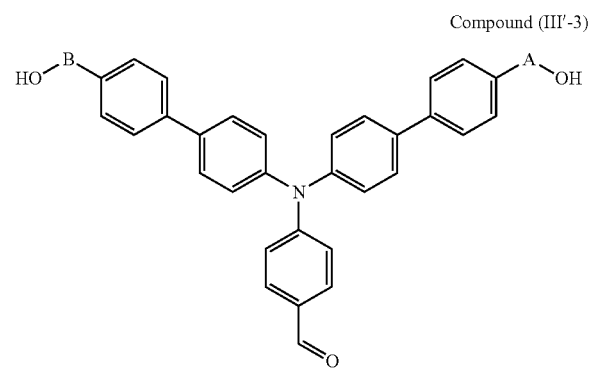

Compound (III'-3)

According to one embodiment, the preferred compound of formula (III'-3) is 4-(bis(4'-(1-hydroxyethyl)-[1,1'-biphenyl]-4-yl)amino)benzaldehyde:

Compound (III'-3a)

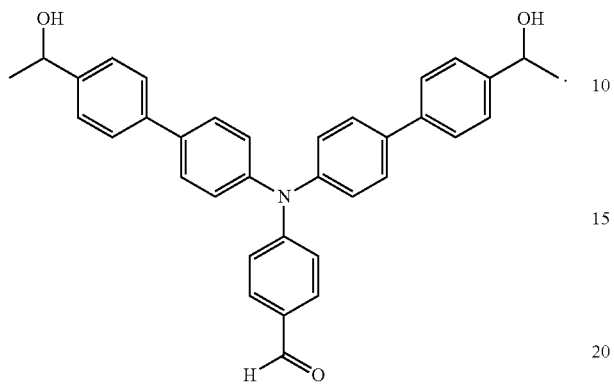

According to one embodiment, the step (i) or the step (ii) further comprises a step of modifying the aldehyde group. According to an embodiment, the step (i) or the step (ii) further comprises a step of modifying the aldehyde group aiming to provide an electron-withdrawing group different from the initial aldehyde group; preferably, said electron-withdrawing group is a dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

According to one embodiment, the step (i) or the step (ii) further comprises a step of modifying the aldehyde group with malononitrile. According to one embodiment, the step (i) further comprises a step of modifying the aldehyde group into a dicyanovinylidene group.

According to one embodiment, the step (i) or the step (ii) further comprises a step of modifying the aldehyde group with an oxidant; preferably, with silver oxide. According to one embodiment, the step (i) or the step (ii) further comprises a step of modifying the aldehyde group into a carboxylic acid group, said carboxylic group furthermore able to be modified with an organic compound comprising at least one photopolymerizable group selected from at least one acryloyl, alkylacryloyl, oxetane, alkyloxetane, styryl, allyl, acrylamide, methacrylamide or cinnamate. According to an embodiment, the step (i) or the step (ii) further comprises a step of modifying the aldehyde group resulting in an intermediate compound of general formula (III-2bis) or (III-3bis):

Compound (III-2bis)

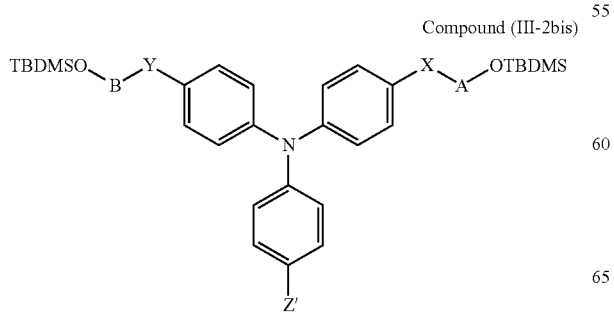

Compound (III-2bis)

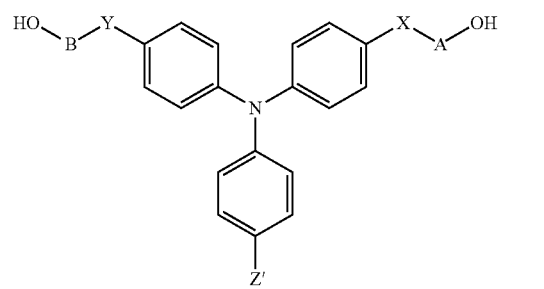

wherein A, B, X and Y are defined as hereinabove, and Z' represents an electron-withdrawing group; preferably, a dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

According to one embodiment, the preferred compounds of formula (III-3bis) are the compounds of general formula (III'-3bis):

Compound (III'-3bis)

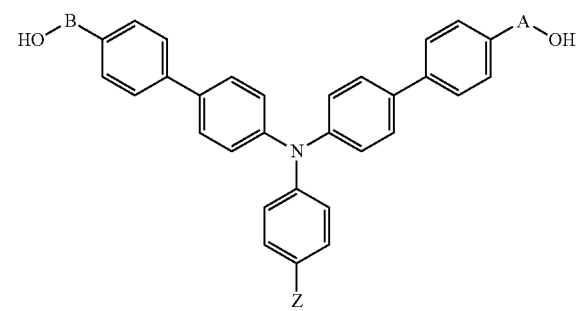

According to one embodiment, the preferred compound of formula (III'-3bis) is 2-(4-(bis(4'-(1-hydroxyethyl)-[1,1'-biphenyl]-4-yl)amino)benzylidene)malononitrile:

Compound (III'-3bis)

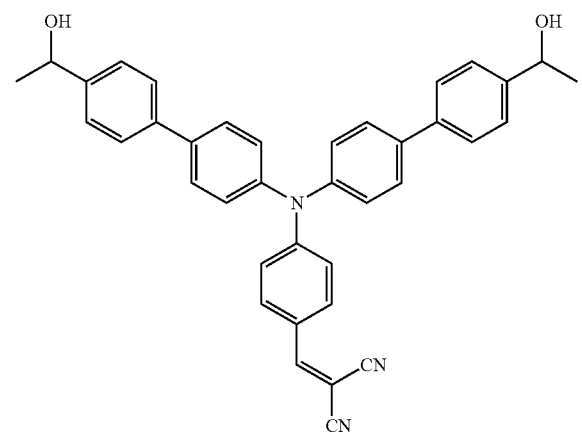

According to one embodiment, the preferred compound of formula (III'-3bis) is 4-(bis(4'-(1-hydroxyethyl)-[1,1'-biphenyl]-4-yl)amino)benzoic acid:

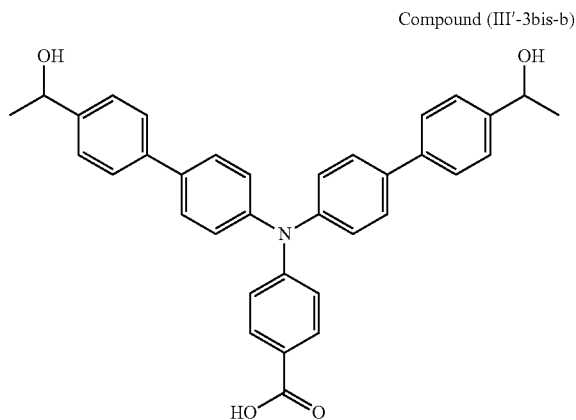 [SMILES: CC(O)c1ccc(-c2ccc(N(c3ccc(C(=O)O)cc3)c3ccc(-c4ccc(C(C)O)cc4)cc3)cc2)cc1]

Compound (III'-3bis-b)

According to one embodiment, the step (iv) comprises the reaction of a compound of general formula (III-3) or (III'-3) having at least one photopolymerizable compound of formula (IV):

T-L-COOH    Formula (IV)

wherein

L represents an alkyl group comprising 1 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; preferably, L represents an alkyl group comprising 3 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group; more preferentially, L represents an alkyl chain interrupted by at least one oxygen atom and substituted with at least one oxo group;

T represents a photopolymerizable group selected from at least one acryloyl, alkylacryloyl, oxetane, alkyloxetane, styryl, allyl, acrylamide, methacrylamide, cinnamate; preferably, T represents an acryloyl group or an alkyloxetane group.

According to one embodiment, the photopolymerizable compound is selected from 4-(2-(acryloyloxy)ethoxy)-4-oxobutanoic acid, 4-(2-(methacryloyloxy)ethoxy)-4-oxobutanoic acid, 4-((3-ethyloxetan-3-yl)methoxy)-4-oxobutanoic acid, 4-((2-(acryloyloxy)ethyl)amino)-4-oxobutanoic acid, 4-((2-(methacryloyloxy)ethyl)amino)-4-oxobutanoic acid, 4-(((3-ethyloxetan-3-yl)methyl)amino)-4-oxobutanoic acid. In one embodiment, the photopolymerizable compound is 4-(2-(acryloyloxy)ethoxy)-4-oxobutanoic acid and/or 4-((3-ethyloxetan-3-yl)methoxy)-4-oxobutanoic acid.

According to one embodiment, the reaction steps (i), (ii), (iii) and (iv) are each independently implemented in organic solvents such as but not limited to hydrocarbons, such as cyclohexane or methylcyclohexane, petroleum ether, toluene or xylene; chlorinated hydrocarbons, such as 1,2-dichloroethane, trifluoromethylbenzene, chloroform or dichloromethane; hydroxyls, such as methanol, ethanol, isopropanol, n-propanol, n-butanol; ethers, such as diethylether, diisopropylether, 2-methyltetrahydrofuran; tetrahydrofuran (THF) or dioxane; ketones, such as acetone or butanone; amides, such as acetamide, dimethylacetamide, N-methylpyrrolidone (NMP) or dimethylformamide (DMF); nitriles, such as acetonitrile; carbon disulfide; carboxylic acids, such as formic acid or acetic acid; esters, such as ethyl acetate, alone or in a mixture, propylene carbonate. In one embodiment, the organic solvents are green solvents. In one embodiment, the organic solvents are anhydrous solvents.

In one embodiment, at least one of the reaction steps (i), (ii), (iii) or (iv) is implemented in dichloromethane. In one embodiment, at least one of the reaction steps (i), (ii), (iii) or (iv) is implemented in anhydrous dichloromethane.

According to one embodiment, the method is carried out at a temperature between 0° C. and 70° C. In one embodiment, the method is carried out at ambient temperature.

According to one embodiment, at least one of the steps (i), (ii), (iii) or (iv) is implemented at a temperature between 0 and 70° C. In one embodiment, at least one of the steps (i), (ii), (iii) or (iv) is implemented at ambient temperature.

According to one embodiment, the reaction of at least one of the steps (i), (ii), (iii) or (iv) is carried out for at least 4 h; preferably, at least 12 h. In one embodiment, the reaction of the step (i) is carried out for 12 h. In one embodiment, the reaction of the step (ii) is carried out for 4 h. In one embodiment, the reaction of the step (iii) is carried out for 12 h. In one embodiment, the reaction of the step (iv) is carried out for 12 h.

According to one embodiment, the reaction of at least one of the steps (i), (ii), (iii) or (iv) is carried out in an inert atmosphere; preferably, under argon or nitrogen.

According to one embodiment, at least one of the steps (i), (ii), (iii) or (iv) has a yield greater than or equal to 40%; preferably, greater than or equal to 50%; preferably, greater than or equal to 60%; preferably, greater than or equal to 80%. In one embodiment at least one of the steps (i), (ii), (iii) or (iv) has a yield greater than or equal to 80%.

According to one embodiment, the step (i) further comprises the use of a phosphine; preferably, tris-o-tolylphosphine.

According to one embodiment, the step (iv) further comprises the use of 4-dimethylaminopyridinium p-toluene sulfonate (DPTS).

According to one embodiment, the step (iv) further comprises the use of a carbodiimide derivative; preferably, N,N'-dicyclohexylcarbodiimide (DCC).

According to one embodiment, the compounds obtained by the method of the invention are stored in an inert atmosphere. According to one embodiment, the compounds obtained by the method of the invention are kept away from light. According to one embodiment, the compounds obtained by the method of the invention are stored at cold temperatures; preferably, between 2 and 8° C.

Uses

This present invention also relates to the use of the compounds of the invention in the field of organic electronics, organic optoelectronics or organic photonics. In particular, the compounds of the invention are useful as precursors of insoluble emissive thin layers, more preferably, for their use in multilayer photonic or electronic devices.

According to one embodiment, this invention relates to the use of the compound of formula (I) or of an intermediate compound of the invention in the field of organic electronics. In one embodiment, this invention relates to the use of the compound of formula (I) or of an intermediate compound of the invention in the field of organic photonics.

Method for Manufacturing a Film

The present invention relates to a method for manufacturing a monomer photo-crosslinkable film having emission properties in the visible range. In particular, the present invention relates to a method for manufacturing a substrate coated with a thin, amorphous, emissive, photo-crosslinkable and non-doped small molecule-based film, comprising the following steps:
  a) providing a composition comprising at least one compound of general formula (I) and/or (II), a solvent and a photoinitiator;
  b) depositing the composition obtained in a) onto a substrate.

In one embodiment, said film is constituted exclusively of the compounds of the invention in the solid state. In one embodiment, the method further comprises a synthetic step of compounds of general formula (I) and/or of general formula (II).

In one embodiment, the composition of the step a) comprises at least one compound of general formula (II). According to one preferred embodiment, the composition comprises compounds of formula (II-a), (II-b), (II-c), (II-d), (II-e) or (II-f). According to one preferred embodiment, the composition comprises the compound of formula (II-a) and the compound of formula (II-b). According to one preferred embodiment, the composition comprises the mixture of at least two compounds selected from the compounds (II-a), (II-b), (II-c), (II-d), (II-e) or (II-f).

In one embodiment, the composition of step a) comprises at least one compound of general formula (I). In one preferred embodiment, the composition comprises at least one compound of formula (I) and the compound of formula (II-a). In one preferred embodiment, the composition comprises at least one compound of formula (I) and the compound of formula (II-b). In one preferred embodiment, the composition comprises at least one compound of formula (I), the compound of formula (II-a) and the compound of formula (II-b). In one preferred embodiment, the composition comprises at least one compound of formula (I) and at least one compound selected from the compounds (II-a), (II-b), (II-c), (II-d), (II-e) or (II-f).

In one embodiment, the solvent is preferably an organic solvent.

In one embodiment, the weight concentration in compounds of the invention is comprised in a range from 0.1 to 10 wt. % to the total weight of the composition; preferably, the weight concentration in compounds of the invention is about 1 wt. %.

In one embodiment, the deposition step may be implemented by a machine or by hand. In one embodiment, the deposition step is carried out in solution. In one embodiment, the deposition step may be implemented by at least one of the techniques selected from spraying, inkjet depositing, spin coating or application with a brush.

In one embodiment, the deposition step is preferably implemented by the technique of spin coating.

According to one embodiment, spin coating is carried out at an angular acceleration less than 1000 rpm/min; preferably, ranging from 200 to 1000 rpm/min; more preferably, the angular acceleration is about 500 rpm/min.

According to one embodiment, the spin coating is carried out at a rotation speed less than 6000 rpm; preferably from 500 to 3000 rpm; more preferably, the rotation speed is about 1000 rpm.

According to one embodiment, the rotation of the substrate whereon the composition has been deposited via spin coating is carried out for less than 10 min; preferably, from 10 s to 300 s; more preferably, the rotation time is about 60 s.

In one embodiment, the substrate is an organic, metal or mineral material; preferably, the substrate is a glass slide or a polymer.

According to one embodiment, the substrate is transparent. According to one embodiment, the substrate is flexible.

According to one embodiment, said film further comprises a dopant.

Method for Manufacturing Emissive (Multi-) Layer

The present invention also relates to a method for manufacturing a photo-crosslinked emissive organic layer or a photo-crosslinked emissive multilayer system comprising the following steps:
  a') implementing the method of manufacturing a substrate coated with a photo-crosslinkable emissive film as described above; then
  b') the photopolymerization of said film;
  c') optionally, repeating steps a') and b'), resulting in an insoluble emissive multilayer device.

In one embodiment, the photopolymerization of step b') includes a photo-crosslinking.

In one embodiment, the photopolymerization is carried out without heating. In one embodiment, the photopolymerization is carried out at room temperature.

According to one embodiment, said method further comprises a step c') of repeating steps a') and b') resulting in a photo-crosslinked emissive multilayer system. According to one embodiment, the photopolymerization of the step b' or c') is carried out using the composition of the compounds of the invention in solid form. According to one embodiment, the photopolymerization of step b' or c') is carried out without residual solvent.

In one embodiment, the photopolymerization performed in step b') or c') is induced by the irradiation of the organic deposit carried out in the step a'). In one embodiment, irradiation is carried out by a white light source, and light-emitting diode or a laser. In one embodiment, irradiation is carried out by a white light source or a laser. In one embodiment, irradiation is carried out by a filtered white light source. In one embodiment, irradiation is carried out at one or several wavelengths between 250 nm and 700 nm; preferably, a wavelength of 365 nm.

In one embodiment, irradiation is carried out at a single wavelength. In one embodiment, irradiation of a mixture of the compounds of the invention is carried out at a single wavelength.

In one embodiment, irradiation is carried out at a power comprised in a range from 1 to 100 mW/cm$^2$. In one embodiment, irradiation is carried out at a power of about 30 mW/cm$^2$. In one embodiment, irradiation is carried out at a power of about 3.5 mW/cm$^2$.

In one embodiment, the duration of irradiation is comprised in a range from 10 to 2000 s; preferably the duration of irradiation is about 1800 s.

In one embodiment, the photopolymerization temperature is comprised in a range from 25 to 50° C.; preferably, the photopolymerization temperature is about 25° C.

According to an embodiment, the photopolymerization of the organic deposit carried out in the step b') results in the formation of an organic thin layer. In one embodiment, the organic thin layer has a thickness comprised in a range from 20 to 500 nm; preferably, the thickness of the organic thin layer is about 130 nm.

According to an embodiment, the photopolymerization of the organic deposit carried out in the step b') results in the formation of an amorphous organic layer for temperatures comprised in a range from −20° C. to 200° C. In one embodiment, the amorphous organic layer is a polymerized organic material.

According to one embodiment, the emissive organic layer has a quantum yield in a range from 0.1 to 1; preferably, greater than 0.1; preferably, greater than 0.2. In one embodiment, the quantum yield of fluorescence is about 0.28.

According to one embodiment, the organic layer is insoluble; in particular with respect to the later deposits.

Method for Manufacturing Fluorescent Nanoparticles

The present invention relates to a method for manufacturing a fluorescent nanoparticle having emission properties in the visible range, comprising the following steps:
a) providing at least one solution comprising at least one compound of general formula (I) and/or (II), a solvent and a photoinitiator; and
b) adding the solution (a) into an aqueous solution under stirring.

According to one embodiment, the solution of the step (a) comprises at least one compound selected from compounds (II-a), (II-c) and/or (II-d). According to one embodiment, the solution of the step (a) comprises a mixture of compounds (II-a), (II-c) and/or (II-d).

According to one embodiment, the step (a) comprises providing a solution comprising compounds of formula (II-a) and another solution comprising compounds of formula (II-c). According to one embodiment, the step (a) comprises providing a solution comprising compounds of formula (II-a) and another solution comprising compounds of formula (II-d). According to one embodiment, the step (a) comprises providing a solution comprising compounds of formula (II-c) and another solution comprising compounds of formula (II-d).

According to one embodiment, in step a), the compound of formula (I) and/or (II) is at a concentration in the solvent, ranging from 0.05 to 5 mg/mL; preferably, from 0.5 to 2 mg/mL; more preferably, the concentration of compound of formula (I) and/or (II) is about 1 mg/mL.

According to one embodiment, the photoinitiator is selected from 2-tert-butylanthraquinone, camphorquinone, diphenyl(2,4,6-trimethylbenzoyl)phosphine oxide, 9,10-phenanthrenequinone, phenylbis(2,4,6-trimethylbenzoyl) phosphine oxide, 2-benzyl-2-(dimethylamino)-4'-morpholinobutyrophenone, 3,6-bis(2-methyl-2-morpholinopropionyl)-9-octylcarbazole, 4'-tert-butyl-2',6'-dimethylacetophenone, 2,2-diethoxyacetophenone, 4'-ethoxyacetophenone, 3'-hydroxyacetophenone, 4'-hydroxyacetophenone, 1-hydroxycyclohexylphenylcetone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, benzoin, benzoinethyl ether, benzoinmethyl ether, 4,4'-dimethylbenzoin, 4,4'-dimethylbenzile, benzophenone, benzoyl biphenyl, 4,4'-bis(diethylamino)benzophenone, 4,4'-dihydroxybenzophenone, 3,4-dimethylbenzophenone, 3-hydroxybenzophenone, 4-hydroxybenzophenone, 2-methylbenzophenone, 3-methylbenzophenone, 4-methylbenzophenone, methyl benzoylformate, Michler's ketone, 1-chloro-4-propoxy-9H-thioxanthen-9-one, 2-chlorothioxanthen-9-one, 2,4-diethyl-9H-thioxanthen-9-one, isopropyl-9H-thioxanthen-9-one, 10-methylphenothiazine, thioxanthen-9-one, diaryliodonium hexafluorophosphate salt, diaryliodonium hexafluoroantimonate salt, triarylsulfonium hexafluorophosphate salt, hexafluorophosphate, triarylsulfonium hexafluoroantimonate salt. In one embodiment, the photoinitiator is diphenyl(2,4,6-trimethylbenzoyl)phosphine oxide (TPO).

According to one embodiment, the concentration of the photoinitiator ranges from 0.1 to 20%; preferably, from 1% to 15%; more preferably, the concentration of the initiator is 10% mol. with respect to the concentration of the compound of general formula (I) and/or (II).

According to one embodiment, the fluorescent nanoparticle may be obtained by a microfluidic process. In one embodiment, the microfluidic process comprises the use of at least one syringe pump. In one embodiment, the microfluidic process comprises the use of colinear tubings, an injection needle and three syringe pumps. In one embodiment, the flow of the microfluidic process ranges from 0.1 $\mu L \cdot min^{-1}$ to 300 $\mu L \cdot min^{-1}$; preferably, from 1 $\mu L \cdot min^{-1}$ to 150 $\mu L \cdot min^{-1}$; more preferably, the flow is about 10 $\mu L \cdot min^{-1}$, 40 $\mu L \cdot min^{-1}$ and/or 100 $\mu L \cdot min^{-1}$. In one embodiment, the flow of the syringe ranges from 0.1 $\mu L \cdot min^{-1}$ to 300 $\mu L \cdot min^{-1}$; preferably, from 1 $\mu L \cdot min^{-1}$ to 150 $\mu L \cdot min^{-1}$; more preferably, the flow is about 10 $\mu L \cdot min^{-1}$, 40 $\mu L \cdot min^{-1}$ and/or 100 $\mu L \cdot min^{-1}$. In one embodiment, the microfluidic process comprises the use of more than one syringe pump, wherein each syringe has a flow ranging from 0.1 $\mu L \cdot min^{-1}$ to 300 $\mu L \cdot min^{-1}$; preferably, from 1 $\mu L \cdot min^{-1}$ to 150 $\mu L \cdot min^{-1}$; more preferably, the flow is about 10 $\mu L \cdot min^{-1}$, 40 $\mu L \cdot min^{-1}$ and/or 100 $\mu L \cdot min^{-1}$.

According to one embodiment, the method for manufacturing the fluorescent nanoparticles further comprises a step of photopolymerization.

In one embodiment, the photopolymerization is carried out under inert atmosphere; preferably under argon or nitrogen.

In one embodiment, the photopolymerization is carried out with a UV lamp; preferably, equipped with a 365 narrow bandpass filter and a quartz light guide.

In one embodiment, the photopolymerization is carried out during a period ranging from 5 s to 180 s; preferably, from 10 s to 60 s; more preferably, during a period of about 30 seconds.

BRIEF DESCRIPTION OF THE DRAWINGS

FIG. 9 depicts the profile of organic layers after polymerization at an irradiation power of 450 mW·cm−2 for 1 min.

EXAMPLES

Figure 1A:
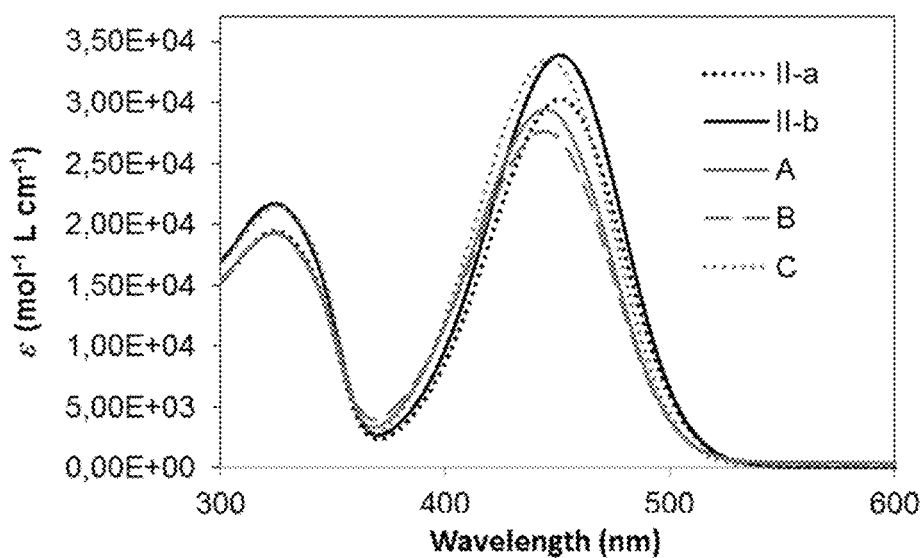
FIG. 1 relates to the absorption spectra of compounds II-a, II-b, A, B and C (FIG. 1A) or compounds II-a, II-c and II-d (FIG. 1B) in toluene solution.

The present invention is further illustrated by the following examples.

A. Material and Methods

Abbreviations

DCC: dicyclohexylcarbodiimide
DEAD: diethylazodicarboxylate
DIPC: N, N-diisopropylcarbodiimide
DMF: dimethylformamide
DPTS: dimethylaminopyridinium p-toluenesulfonate
DSC: Differential Scanning Calorimetry
MeOH: methanol
NHE: Normal Hydrogen Electrode
RT: room temperature
SDS: sodium dodecylsufate
TBAF: tetrabutylammonium fluoride
TBDMS: tert-butyldimethylsilyl group
TBDMSCl: tert-butyldimethylsilyl chloride
TEM: Transmission Electronic Microscopy
THF: tetrahydrofuran
TMS: tetramethylsilane
TPO: phenylbis(2,4,6-trimethylbenzoyl)phosphine oxide
Reagents All chemical reagents and solvents were purchased from commercial sources (Aldrich, Acros, SDS) and used as received. Spectroscopic grade solvents purchased from Aldrich were used for spectroscopic measurements. All air-sensitive reactions were performed under argon using a vacuum line. Analytical TLC was performed on Kieselgel F-254 precoated plates. Visualization was done with UV lamp. Flash chromatography was carried out with silica gel 60 (230-400 mesh) from SDS and 4-bis(4'-tert-butylbiphenyl-4-yl)aminobenzaldehyde was synthesized according to literature procedures (Ishow et al., Chem. Mater. 2008, 20, 6597-6599).

Photopolymerization
Substrate

All polymerization tests were carried out on organic film deposited on glass substrates that were previously cleaned by successive treatments in a wave bath with an alkaline solution (2% Hellmanex), with distilled water and then, absolute ethanol. Each washing step was implemented during 10 min. The glass substrate was then dried under nitrogen flux and stored in an inert atmosphere.

All solutions for depositions implementation were carried out with spectroscopic grade chloroform in order to provide thin layers without micro aggregates.

Physico-Chemical Analysis
Nuclear Magnetic Resonance Spectroscopy (NMR)

$^1$H NMR and $^{13}$C NMR spectra were recorded on Bruker 300 MHz or 400 MHz spectrometers. Chemical shifts δ were reported in ppm relative to TMS and referenced to the residual solvent.

Mass Spectrometry

Low-resolution mass (LR-MS) spectra were obtained by electrospray ion trap mass spectrometry (LC-Esquire, Bruker) in positive-ion mode. High-resolution mass (HR-MS) spectra were obtained either by electrospray ionization coupled with high resolution ion trap orbitrap (LTQ-Orbitrap, ThermoFisher Scientific) or by MALDI-TOF-TOF (Autoflex III de Bruker), both working in ion-positive mode.

UV-Visible Absorption Spectroscopy

Spectroscopic grade solvents have systematically been used for photophysical studies and the fabrication of thin films. UV-visible absorption spectra were recorded using a Varian Model Cary 5E spectrophotometer.

Steady-State Fluorescence Spectroscopy

Corrected emission spectra were obtained using Jobin-Yvon. Inc spectrofluorimeter (Fluorolog 3 equipped with right-angle and front-face configurations for solution and thin films measurements, respectively). Fluorescence quantum yields in solution were determined from fluorescence standard using Coumarine 540 A in ethanol ($\Phi_f$=0.38) or POPOP in cyclohexane ($\Phi_f$=0.38).

Time-Resolved Fluorescence Spectroscopy

Fluorescence intensity decays were measured by the time-correlated single-photon counting method (TCSPC) using the TimeHarp 260 PICO TCSPC module implemented on the FluoTime 300 "EasyTau" fluorescence lifetime spectrometer purchased from Picoquant. Excitation was performed with a picosecond pulsed laser diode at 450±10 nm (FWHM>70 ps) at magic angle. Fluorescence photons were detected at the emission maximum through a monochromator by means of a Hybrid-PMT (PMA Hybrid 40, Picoquant) with an instrument response of 120 ps and connected to a constant-fraction discriminator.

Infrared Absorption Spectroscopy

Potassium bromide monocrystals were used as infrared substrates to investigate the photopolymerization reaction of spin-coated thin films. The spectra were recorded as a function of time under a flow of nitrogen using an infrared Bruker Tensor 27 spectrometer.

Transmission Electron Microscopy (TEM)

Transmission Electron Microscopy imaging was performed using the MO-Jeol 1230 (80 kV) electron microscope. Aqueous solutions of nanoparticles were deposited onto copper grids (300 mesh) coated with carbon thin films and lacey carbon copper grids (300 mesh).

Photoirradiation

Photoirradiation was performed using a continuous Hg—Xe white source lamp (Hamamatsu—LC8) equipped with a bundle of quartz fibers and a collimator. The irradiation was selected by means of a narrow band filter at 365 nm (Semrock, Hg-01-365-25, 12 nm bandwith) with a high transmittance Tav (>93%).

Thermal Analyses

Glass transition temperatures were obtained using differential scanning calorimetry (DSC) (Maia 205 C—Netzsch) in aluminum caps under a nitrogen flow at a scan rate of 30° C.·min$^{-1}$ over the temperature range from −30° C. to 140° C. after a first heating-cooling cycle to erase the thermal history of the sample.

B. Synthesis of Compounds of Formula (II)

B.1. Synthesis of Compounds of Formula II-a and II-b

The synthesis of compounds of formula II-a to II-f is performed according to the following procedures (see schemes 1, 2 and 3).

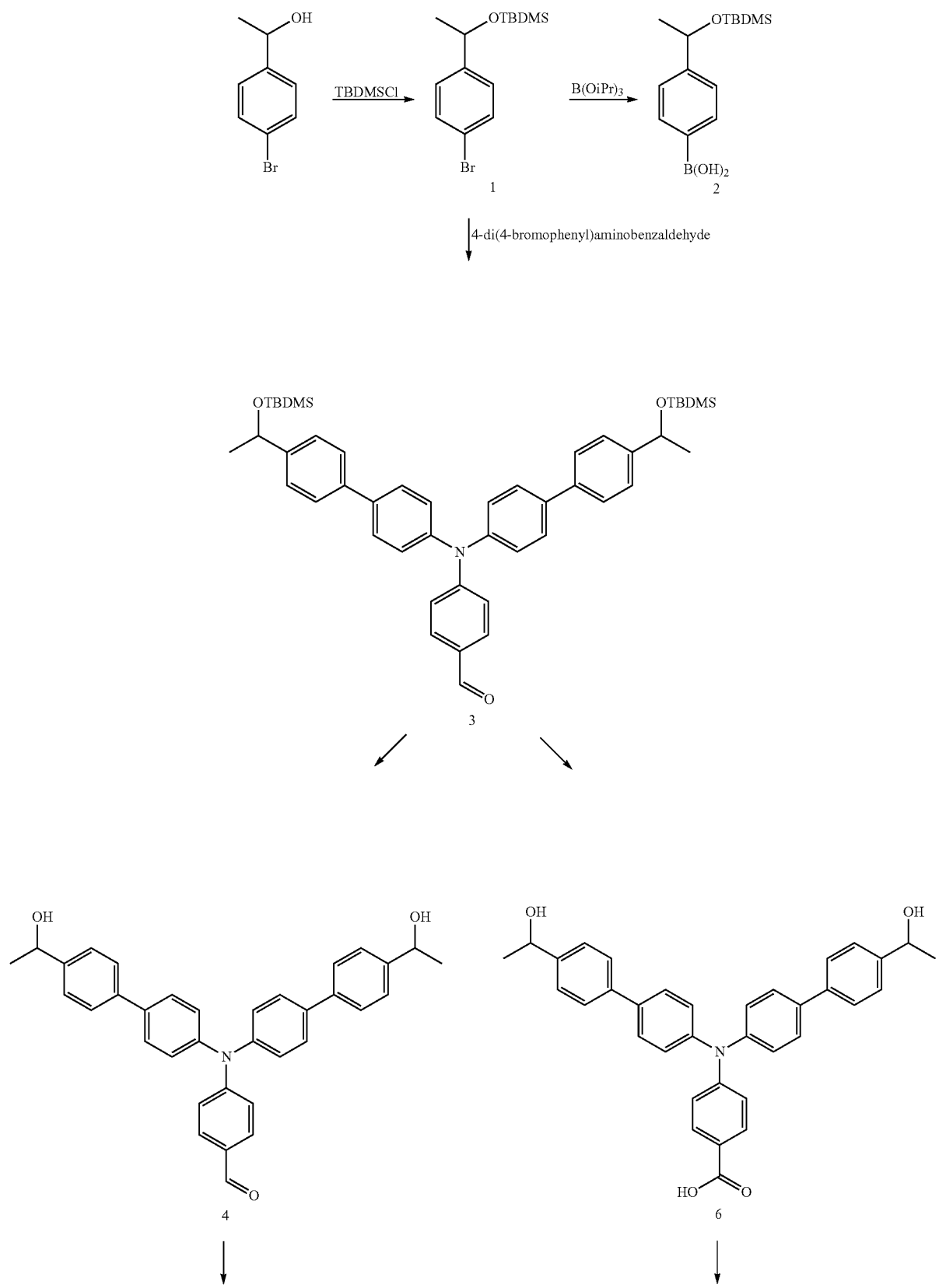
Scheme 1. Synthesis of triarylamine core.

-continued
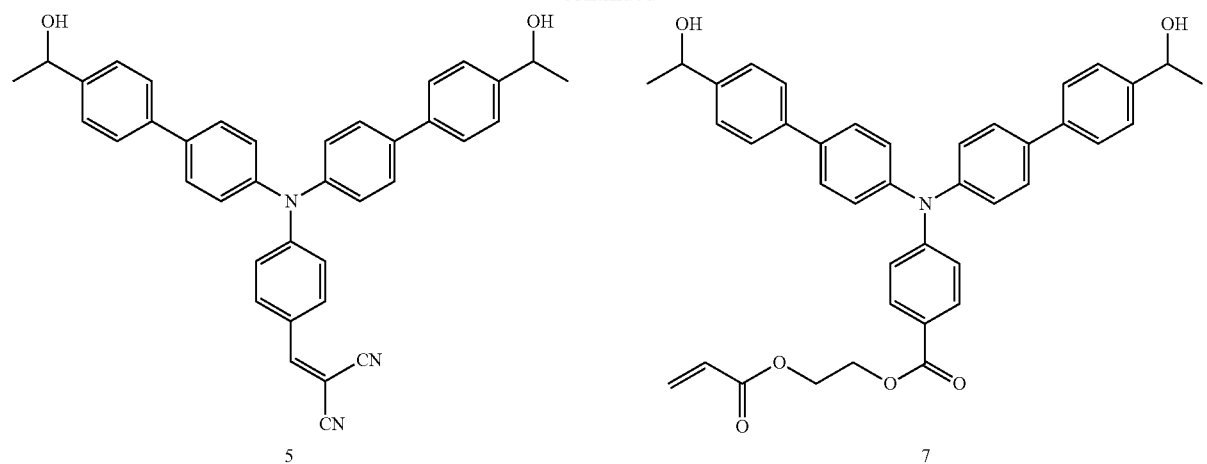 [SMILES: CC(O)c1ccc(-c2ccc(N(c3ccc(C=C(C#N)C#N)cc3)c3ccc(-c4ccc(C(C)O)cc4)cc3)cc2)cc1 ; C=CC(=O)OCCOC(=O)c1ccc(N(c2ccc(-c3ccc(C(C)O)cc3)cc2)c2ccc(-c3ccc(C(C)O)cc3)cc2)cc1]
Scheme 2. Introduction of spacers comprising acryloyl photopolymerizable groups.
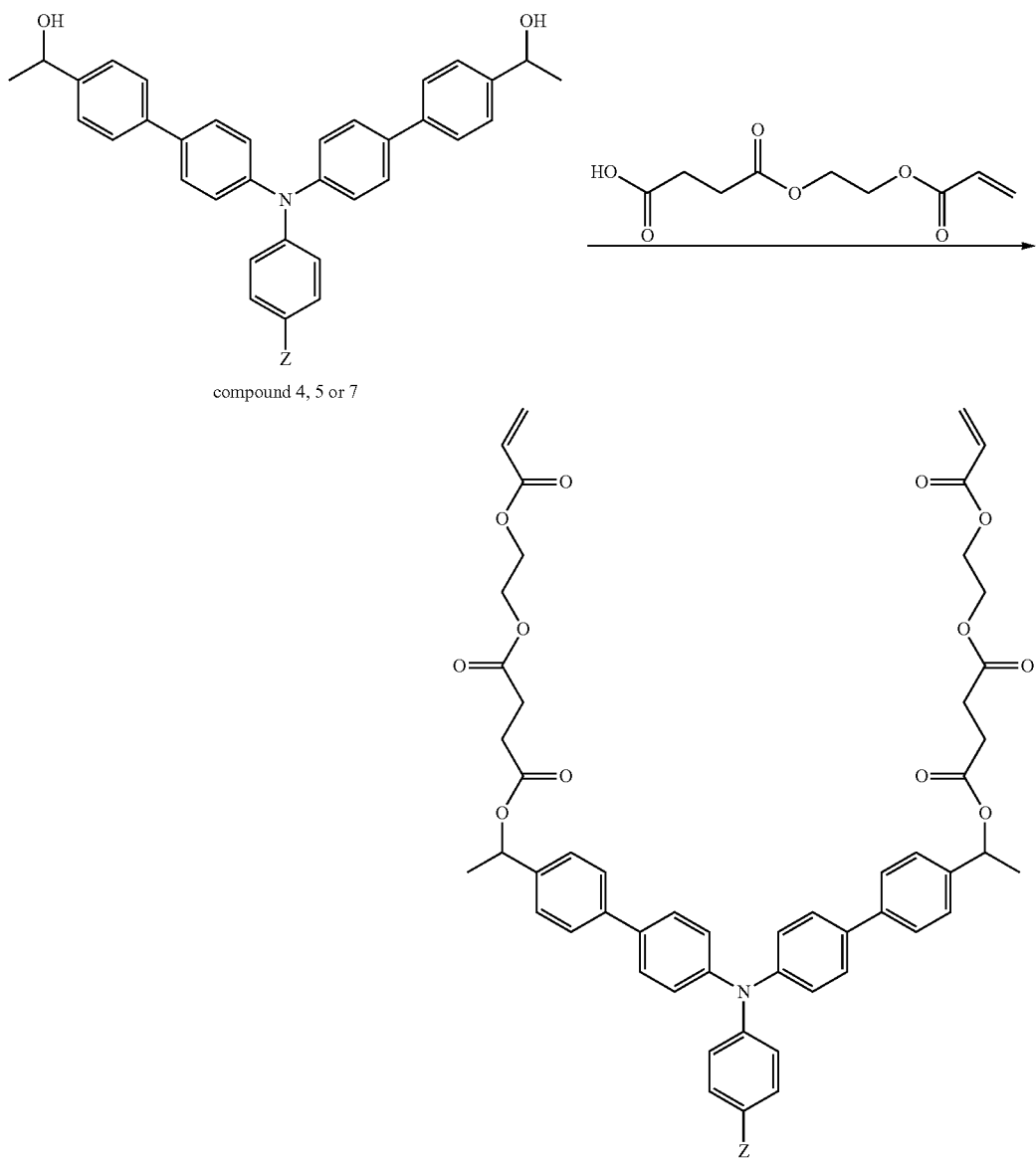
compound 4, 5 or 7

-continued

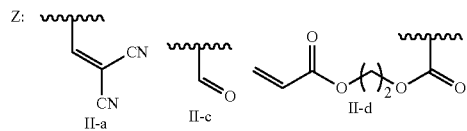

Scheme 3. Introduction of spacers comprising oxetan photopolymerizable groups.

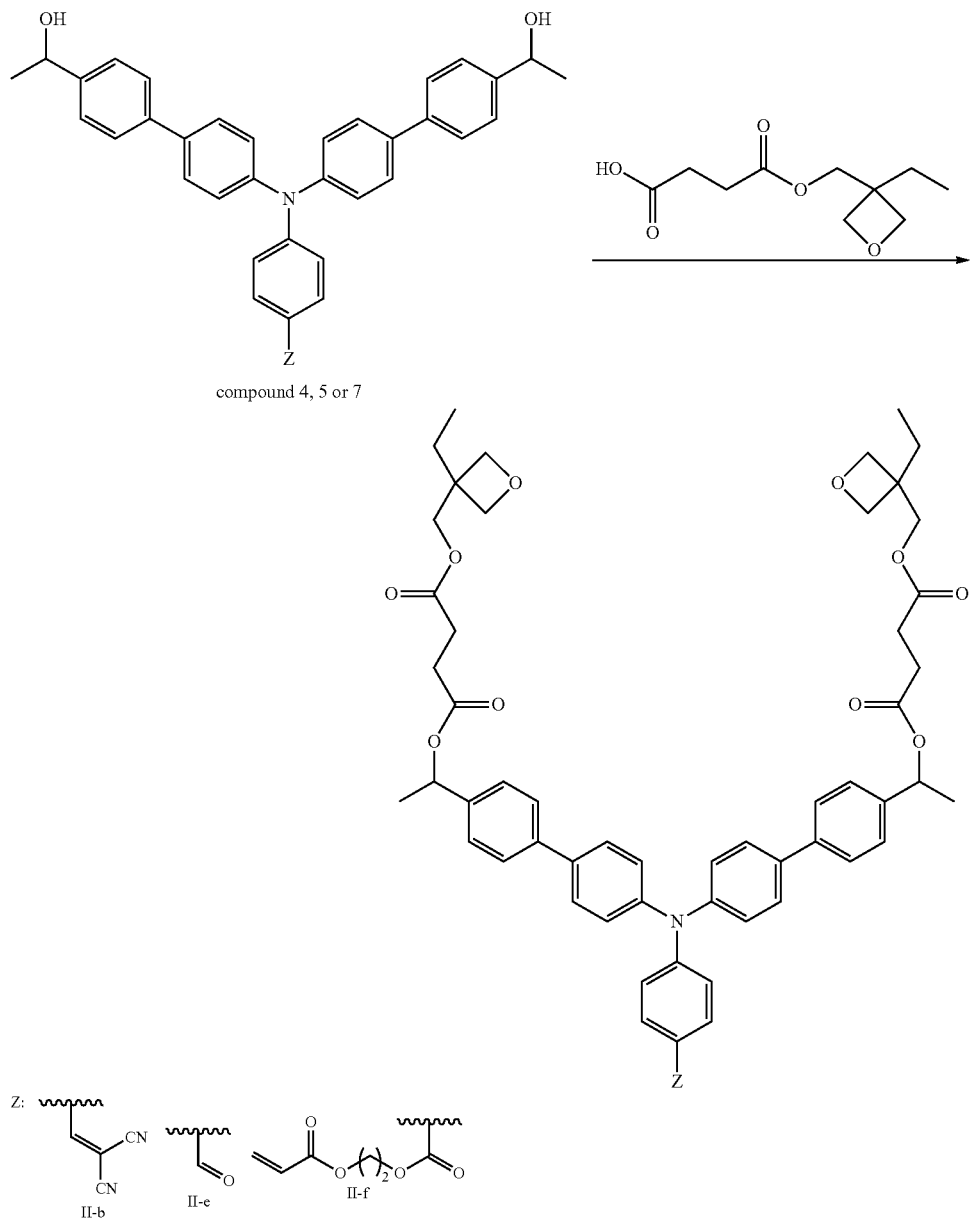

B.1.1. Synthesis of Intermediate Products

Intermediate 1: 1-bromo-4-{1-[(tert-butyldimethyl-silyl)oxy]ethyl}benzene 4-bromo-α-methylbenzyl alcohol (1.7 g, 8.46 mmol, 1 eq.) and dimethylaminopyridine (catalytic amount) were first dissolved in anhydrous dimnethylformnnamide (10 mL). After addition of imidazole (1.73 g, 10.1 mmol, 1.2 eq.), t-butyl-dimethylsilyl chloride (1.51 g, 10.1 mmol, 1.2 eq.) was added. The reaction mixture was stirred at room temperature under argon for 2 days. After dilution with dichloromethane, the organic layer was extracted, washed four times with brine, dried over anhydrous $Na_2SO_4$, and concentrated under vacuum. The resulting pale yellow oil was purified by silica gel chromatography using petroleum ether:dichloromethane 1:1 as an eluent. Compound 1 was obtained as a colorless oil. (2.16 g, 81%).

$^1$H NMR (CDCl$_3$, 300 MHz): δ=7.42 (d, $^3$J=8.5 Hz, 2H), 7.20 (d, $^3$J=8.5 Hz, 2H), 4.81 (q, $^3$J=6.3 Hz, 1H), 1.37 (d, $^3$J=6.4 Hz, 3H), 0.89 (s, 9H), 0.04 (s, 3H), −0.04 (s, 3H) ppm.

$^{13}$C NMR (CDCl$_3$, 75 MHz): δ=146.0, 131.2, 127.0, 120.4, 70.3, 27.2, 25.8, 18.1, −2.9, −4.9 ppm.

Intermediate 2: 4-{1-[(tert-butyldimethylsilyl)oxy]ethyl}phenyl boronic acid

A solution of compound 1 (3.1 g, 9.84 mmol, 1 eq.) in anhydrous tetrahydrofuran (20 mL) was cooled to −80° C. before adding a 1.6 M n-butyllithium solution in hexane (8 mL, 12.8 mmol, 1.3 eq.) dropwise. The resulting mixture was stirred for 1 h at −80° C. and triisopropylborate (9 mL, 39.4 mmol, 4 eq.) was added portionwise over 30 min. The solution was slowly warmed up to room temperature over 3 h and stirred a further hour at room temperature. Excess of n-butyllithium was neutralized with a 1 M HCl solution until pH=3-4. The organic layer was washed twice with brine, dried over anhydrous Na$_2$SO$_4$, and concentrated under vacuum. The resulting colorless oil (2.71 g, 97%) was used without further purification.

$^1$H NMR (CDCl$_3$, 300 MHz): δ=8.19 (d, $^3$J=8.1 Hz, 2H), 7.47 (d, $^3$J=7.9 Hz, 2H), 4.95 (q, $^3$J=6.3 Hz, 1H), 1.46 (d, $^3$J=6.4 Hz, 3H), 0.93 (s, 9H), 0.08 (s, 3H), 0.00 (s, 3H) ppm.

$^{13}$C NMR (CDCl$_3$, 75 MHz): δ=151.7; 135.6; 124.8; 70.9; 27.2; 25.9; 18.3; −4.8 ppm.

Intermediate 3: 4-{bis[4'-{1-[(tert-butyldimethylsilyl)oxy]ethyl}(1,1'-biphenyl)-4-yl]amino}benzaldehyde 4-di(4-bromophenyl)aminobenzaldehyde (195 mg, 0.46 mmol, 1 eq.), tris-o-tolylphosphine (29 mg, 97 μmol, 21% mol.) and palladium acetate (II) (7 mg, 32 μmol, 7% mol.) were placed in toluene (9 mL) and stirred for 2 min under argon. A solution of boronic acid 2 (326 mg, 1.16 mmol, 2.5 eq.) in deoxygenated methanol (2 mL) was subsequently added, followed by potassium hydroxide (160 mg, 2.8 mmol, 6 eq.) in water (1 mL). The reaction mixture was heated overnight at 70° C. under inert atmosphere. After cooling to room temperature, the extracted organic layer was washed twice with brine, dried over MgSO$_4$, and concentrated under vacuum. Compound 3 was obtained as a yellow solid after purification by silica gel chromatography using with petroleum ether:dichloromethane 1:4 as an eluent (260 mg, 76%).

$^1$H NMR (CDCl$_3$, 300 MHz): δ=9.84 (s, 1H), 7.72 (d, $^3$J=8.7 Hz, 2H), 7.58 (d, $^3$J=8.6 Hz, 4H), 7.55 (d, $^3$J=8.2 Hz, 4H), 7.40 (d, $^3$J=8.2 Hz, 4H), 7.25 (d, $^3$J=8.3 Hz, 4H), 7.13 (d, $^3$J=8.8 Hz, 2H), 4.92 (q, 3J=6.5 Hz, 2H), 1.44 (d, 3J=6.3 Hz, 6H), 0.92 (s, 18H), 0.07 (s, 6H), 0.00 (s, 6H) ppm.

$^{13}$C NMR (CDCl$_3$, 75 MHz): δ=190.6, 153.3, 146.3, 145.3, 138.7, 137.9, 131.5, 129.5, 128.3, 126.7, 126.4, 125.9, 120.0, 70.7, 27.4, 26.0, 18.4, −4.64 ppm.

HRMS (MALDI-TOF) m/z: (M$^+$, 100%) calculated for C$_{47}$H$_{59}$NO$_3$Si$_2$ 742.4106; found 742.4133.

Intermediate 4: 4-{bis[4'-(1-hydroxyethyl) (1,1'-biphenyl)-4-yl]amino}benzaldehyde A solution of compound 3 (280 mg, 0.38 mmol, 1 eq.) in anhydrous tetrahydrofuran (10 mL) and tetrabutylammonium fluoride (1 mL, 1 M, 2.6 eq.) was stirred overnight at room temperature under argon. The solution was washed twice with brine, and the organic layer was dried over anhydrous MgSO$_4$, before solvent removal under vacuum. The crude product was purified by silica gel chromatography using petroleum ether: ethyl acetate 1/1 as an eluent to give compound 4 as a yellow solid (180 mg, 92%).

$^1$H NMR (CDCl$_3$, 300 MHz): δ=9.84 (s, 1H), 7.73 (d, $^3$J=8.8 Hz, 2H), 7.60 (d, $^3$J=3.9 Hz, 4H), 7.57 (d, $^3$J=4.2 Hz, 4H), 7.46 (d, $^3$J=8.2 Hz, 4H), 7.27 (d, $^3$J=8.4 Hz, 4H), 7.15 (d, $^3$J=8.7 Hz, 2H), 4.97 (q, $^3$J=6.3 Hz, 2H), 1.55 (d, $^3$J=6.5 Hz, 6H) ppm.

$^{13}$C NMR (CDCl$_3$, 75 MHz): δ=190.5, 153.1, 145.3, 144.9, 139.5, 137.5, 131.4, 129.5, 128.3, 127.0, 126.3, 125.0, 120.1, 70.2, 25.2 ppm.

HRMS (MALDI-TOF) m/z: (M$^+$, 100%) calculated for C$_{35}$H$_{31}$NO$_3$ 513.2298; found 513.2293.

Intermediate 5: 4-{bis[4'-(1-hydroxyethyl) (1,1'-biphenyl)-4-yl]amino}-1-(2,2-dicyanovinyl)benzene To a solution of compound 4 (350 mg, 0.67 mmol, 1 eq.) in anhydrous pyridine (7 mL) and acetic acid (2 mL) were added a catalytic amount of ammonium acetate, followed by malononitrile (185 mg, 2.8 mmol, 4 eq.). The reaction mixture was stirred overnight at room temperature under argon. After addition of a 1 M HCl solution (5 mL), the red solid was filtered off, and washed with a 1 M HCl solution and distilled water. The red solid was dissolved in dichloromethane, and the resulting solution was dried over anhydrous MgSO$_4$, before solvent removal under vacuum to give compound 5 as a pure red solid (360 mg, 96%).

$^1$H NMR (CDCl$_3$, 300 MHz): δ=7.78 (d, $^3$J=9.0 Hz, 2H), 7.61 (d, $^3$J=6.0 Hz, 4H), 7.58 (d, $^3$J=5.5 Hz, 4H), 7.54 (s, 1H), 7.47 (d, $^3$J=8.2 Hz, 4H), 7.29 (d, $^3$J=8.5 Hz, 4H), 7.08 (d, $^3$J=9.0 Hz, 2H), 4.97 (q, $^3$J=6.4 Hz, 2H), 1.55 (d, $^3$J=6.5 Hz, 6H) ppm.

$^{13}$C NMR (CDCl$_3$, 75 MHz): δ=157.9, 153.2, 145.1, 144.3, 141.8, 139.2, 138.6, 133.1, 128.5, 127.1, 126.8, 126.0, 123.2, 119.1, 75.85, 70.13, 25.24 ppm.

HRMS (MALDI-TOF) m/z: (M$^+$, 100%) calculated for C$_{38}$H$_{31}$N$_3$O$_2$ 561.2411; found 561.2429.

Intermediate 6: 4-(bis(4'-(1-hydroxyethyl)-[1,1'-biphenyl]-4-yl)amino)benzoic acid To a solution of sodium hydroxyde (6.7 g, 169 mmol, 50 eq.) in ethanol (330 mL) thoroughly deoxygenated are added silver oxide (3.12 g, 13.5 mmol, 4 eq.) and a deoxygenated solution of compound 3 (2.5 g, 3.37 mmol, 1 eq.) in anhydrous toluene (24 mL). The reaction mixture was stirred under inert atmosphere for 12 h, and further neutralized with a 3 mol·L$^{-1}$ HCl aqueous solution, added dropwise. This acidic treatment cleaved the tert-butyldimethylsilyl protective groups to generate the carboxylic acid 13 in one step. After one hour of stirring, the product was extracted with ethylacetate, washed once with distilled water and dried over anhydrous magnesium sulfate. The solution was filtered and dried under vacuum. A white solid with greenish fluorescence and matching compound 13 formed on the flask and was used readily without requiring further purification (1.77 g, 3.34 mmol, 99%).

$^1$H NMR (CDCl$_3$, 300 MHz): δ=7.90 (d, J=9.0 Hz, 2H), 7.58 (d, J=8.4 Hz, 4H), 7.54 (d, J=8.7 Hz, 4H), 7.45 (d, J=8.1 Hz, 4H), 7.23 (d, J=8.7 Hz, 4H), 7.10 (d, J=8.9 Hz, 2H), 6.44 (dd, J=17.3, 1.5 Hz, 1H), 6.15 (dd, J=17.3, 10.4 Hz, 1H), 5.85 (dd, J=10.4, 1.5 Hz, 1H), 4.96 (q, J=6.4 Hz, 2H), 4.56-4.51 (m, 2H), 4.51-4.45 (m, 2H), 1.54 (d, J=6.5 Hz, 6H) ppm.

$^{13}$C NMR (CDCl$_3$, 75 MHz): δ=166.1, 166.0, 151.9, 145.8, 144.8, 139.6, 136.9, 131.4, 131.1, 128.1, 128.1, 126.9, 125.9, 125.9, 122.1, 120.6, 70.2, 62.4, 62.3, 25.2 ppm.

HR-MS MALDI m/z: [M$^+$] calculated for C$_{35}$H$_{31}$NO$_4$ 529.2248; found 529.2224.

Intermediate 7: 2-(acryloyloxy)ethyl 4-(bis(4'-(1-hydroxyethyl)-[1,1'-biphenyl]-4-yl)amino)benzoate A solution of carboxylic acid derivative 6 (100 mg, 0.19 mmol, 1 eq.), DPTS acidic catalyst (30 mg, 0.1 mmol, 0.5 eq.) and 2-hydroxyethylacrylate (44 μL, 0.28 mmol, 2 eq.) in anhydrous dichloromethane (4 mL) was placed under inert atmosphere and cooled down to 0° C. with an ice bath. The DIPC coupling agent (39 μL, 0.25 mmol, 1.3 eq.) was first diluted in anhydrous dichloromethane (500 μL) and then added dropwise to the reaction mixture. The solution was stirred at room temperature for 12 h before adding saturated sodium chloride solution. The organic layer was extracted, dried over anhydrous sodium sulfate, filtered over a cotton plug, and eventually evaporated to dryness under vacuum. The resulting brown product was purified by silica gel column chromatography using as an eluent a mixture of petroleum ether:ethyl acetate EP/AcOEt 1/1 to yield compound 7 as a white solid, blue-emitting (50 mg, 81.6 μmol, 43%).

$^1$H NMR (CDCl$_3$, 300 MHz): δ=7.90 (d, J=9.0 Hz, 2H), 7.58 (d, J=8.4 Hz, 4H), 7.54 (d, J=8.7 Hz, 4H), 7.45 (d, J=8.1 Hz, 4H), 7.23 (d, J=8.7 Hz, 4H), 7.10 (d, J=8.9 Hz, 2H), 6.44 (dd, J=17.3, 1.5 Hz, 1H), 6.15 (dd, J=17.3, 10.4 Hz, 1H), 5.85 (dd, J=10.4, 1.5 Hz, 1H), 4.96 (q, J=6.4 Hz, 2H), 4.56-4.51 (m, 2H), 4.51-4.45 (m, 2H), 1.54 (d, J=6.5 Hz, 6H) ppm.

$^{13}$C NMR (CDCl$_3$, 75 MHz): δ=166.1, 166.0, 151.9, 145.8, 144.8, 139.6, 136.9, 131.4, 131.1, 128.1, 128.1, 126.9, 125.9, 125.9, 122.1, 120.6, 70.2, 62.4, 62.3, 25.2 ppm.

HR-MS MALDI m/z: [M]+ calculated for C40H37NO6 627.2615; found 627.2600.

B.1.2. Synthesis of Final Compounds

Compound II-a: Bis(2-(acryloyloxy)ethyl) O,O'-(((4-2(2,2-dicyanovinyl)phenyl)azanediyl)bis([1,1'-biphenyl]-4',4-diyl))bis(ethane-1,1-diyl)) disuccinate A solution of 4-(2-(acryloyloxy)ethoxy)-4-oxobutanoic acid (730 mg, 1.30 mmol, 1 eq.), dimethylaminopyridinium p-toluenesulfonate (DPTS) (381 mg, 1.30 mmol, 1 eq.) and compound 5 (1.12 g, 5.2 mmol, 4 eq.) in anhydrous dichloromethane (30 mL) was placed under inert atmosphere and cooled down to 0° C. A solution of dicyclocarbodiimide (DCC) (803 mg, 3.90 mmol, 3 eq.) previously diluted in anhydrous dichloromethane (5 mL) was then added dropwise. The resulting mixture was left under stirring at room temperature for 12 h. After filtration of the solid impurities and concentration of the solution under vacuum, the resulting crude product was dissolved in toluene (~1-3 mL) and filtered to remove undissolved urea. Purification of the reddish power was performed by silica gel chromatography using petroleum ether/ethyl acetate 6/4 as an eluent to provide compound 8 as a honey-like viscous red compound (790 mg, 0.82 mmol, 63%).

$^1$H NMR (CDCl$_3$, 300 MHz): δ=7.78 (d, J=9.0 Hz, 2H), 7.62-7.52 (m, 9H), 7.43 (d, J=8.2 Hz, 4H), 7.28 (d, J=8.2 Hz, 4H), 7.08 (d, J=9.0 Hz, 2H), 6.43 (dd, J=17.3, 1.4 Hz, 2H), 6.13 (dd, J=17.3, 10.4 Hz, 2H), 5.94 (q, J=6.6 Hz, 2H), 5.85 (dd, J=10.4, 1.4 Hz, 2H), 4.39-4.29 (m, 8H), 2.71-2.65 (m, J=4.9 Hz, 8H), 1.58 (d, J=6.8 Hz, 6H) ppm.

$^{13}$C NMR (CDCl$_3$, 75 MHz): δ=173.8, 172.1, 171.4, 165.9, 144.4, 140.8, 139.7, 139.6, 138.4, 133.0, 132.9, 131.5, 128.5, 127.9, 127.1, 126.8, 126.7, 123.3, 119.2, 72.5, 71.1, 62.4, 62.2, 29.4, 29.0, 22.2 ppm.

HR-MS (MALDI-TOF) m/z: [M]$^+$ calculated for C$_{56}$H$_{51}$N$_3$O$_{12}$ 957.3467; found 957.3498.

Compound II-c: Bis(2-(acryloyloxy)ethyl) O,O'-((((4-formylphenyl)azanediyl)bis([1,1'-biphenyl]-4', 4-diyl))bis(ethane-1,1-diyl)) disuccinate A solution of compound 4 (1.42 g, 2.76 mmol, 1 eq.), dimethylaminopyridinium p-toluenesulfonate (DPTS) (811 mg, 2.76 mmol, 1 eq.) and compound 15 (2.39 g, 11 mmol, 4 eq.) in anhydrous dichloromethane (30 mL) was placed under inert atmosphere and cooled down to 0° C. A solution of dicyclocarbodiimide (DCC) (1.7 g, 8.26 mmol, 3 eq.) previously diluted in anhydrous dichloromethane (5 mL) was then added dropwise. The resulting mixture was left under stirring at room temperature for 12 h. After filtration of the solid impurities and concentration of the solution under vacuum, the resulting crude product was dissolved in toluene (~1-3 mL) and filtered to remove undissolved urea. After concentration of the solution, purification of the white solid was performed by silica gel chromatography using dichloromethane as an eluent to yield the photopolymerizable green emitter II-c as a yellow green amorphous solid (1.6 g, 1.76 mmol, 64%).

$^1$H NMR (CDCl$_3$, 300 MHz, δ): 9.84 (s, 1H), 7.73 (d, J=8.8 Hz, 2H), 7.56 (m, 8H), 7.42 (d, J=8.2 Hz, 4H), 7.26 (d, J=8.6 Hz, 4H), 7.14 (d, J=8.7 Hz, 2H), 6.43 (dd, J=17.3, 1.5 Hz, 2H), 6.13 (dd, J=17.3, 10.4 Hz, 1H), 5.94 (q, J=6.6 Hz, 2H), 5.85 (dd, J=10.4, 1.5 Hz, 1H), 4.33 (m, 8H), 2.76-2.62 (m, 8H), 1.58 (d, J=6.5 Hz, 6H) ppm.

$^{13}$C NMR (CDCl$_3$, 75 MHz, δ): 190.4, 172.0, 171.4, 165.8, 153.0, 145.4, 140.5, 139.9, 137.3, 131.4, 131.3, 129.6, 128.3, 127.9, 126.9, 126.6, 126.2, 120.1, 72.5, 62.3, 62.1, 29.3, 28.9, 22.1 ppm.

HR-MS (ESI) m/z: [M]$^+$ calculated for C$_{53}$H$_{51}$NO$_{13}$ 910.3433; found 910.3422.

Compound II-d: ((((4-((2-(acryloyloxy)ethoxy)carbonyl)phenyl)azanediyl)bis([1,1'-biphenyl]-4',4-diyl))bis (ethane-1, 1-diyl))bis(2-(acryloyloxy)ethyl) disuccinate A solution of compound 7 (440 mg, 0.7 mmol, 1 eq.), dimethylaminopyridinium p-toluenesulfonate (DPTS) (206 mg, 0.7 mmol, 1 eq.) and compound 15 (605 mg, 2.8 mmol, 4 eq.) in anhydrous dichloromethane (10 mL) was placed under inert atmosphere and cooled down to 0° C. A solution of dicyclocarbodiimide (DCC) (433 mg, 2.1 mmol, 3 eq.) previously diluted in anhydrous dichloromethane (2 mL) was then added dropwise. The resulting mixture was left under stirring at room temperature for 12 h. After filtration of the solid impurities and concentration of the solution under vacuum, the resulting crude product was dissolved in toluene (~1-3 mL) and filtered to remove undissolved urea. After concentration of the solution, purification of the white solid was performed by silica gel chromatography using as an eluent a mixture ethyl acetate/petroleum ether 1/1, and yielded compound II-d as a pale-green amorphous solid (300 mg, 0.32 mmol, 46%).

$^1$H NMR (CDCl$_3$, 300 MHz): δ=7.90 (d, J=8.9 Hz, 2H), 7.56 (d, J=8.3 Hz, 4H), 7.53 (d, J=8.7 Hz, 4H), 7.41 (d, J=8.3 Hz, 4H), 7.23 (d, J=8.6 Hz, 4H), 7.10 (d, J=8.9 Hz, 2H), 6.45 (dd, J=17.3, 1.5 Hz, 1H), 6.43 (dd, J=17.3, 1.5 Hz, 2H), 6.15 (dd, J=17.4, 10.3 Hz, 1H), 6.13 (dd, J=17.3, 10.4 Hz, 2H), 5.94 (q, J=6.6 Hz, 2H), 5.86 (dd, J=10.4, 1.8 Hz, 1H), 5.85 (dd, J=10.4, 1.5 Hz, 2H), 4.54-4.52 (m, 2H), 4.50-4.47 (m, 2H), 4.36-4.30 (m, 8H), 2.75-2.62 (m, 8H), 1.58 (d, J=6.6 Hz, 6H) ppm.

$^{13}$C NMR (CDCl$_3$, 75 MHz): δ=172.1, 171.4, 166.0, 166.0, 165.9, 151.9, 145.9, 140.4, 140.0, 136.7, 131.4, 131.4, 131.1, 128.2, 128.1, 127.9, 127.0, 126.6, 125.8, 122.3, 120.7, 72.6, 62.4, 62.3, 62.2, 29.4, 29.0, 22.1 ppm.

HR-MS MALDI m/z: [M]$^+$ calculated for C$_{58}$H$_{57}$NO$_{16}$ 1023.3672; found 1023.3661.

C. Studies of Thermal and Photophysical Properties

The thermal and photophysical properties of compounds II-a, II-b, II-c et II-d in solution and processed as thin films have been studied.

Comparative measurements analyses have been performed between compounds II-a up to II-d on one hand, and A, B, C on the other hand:

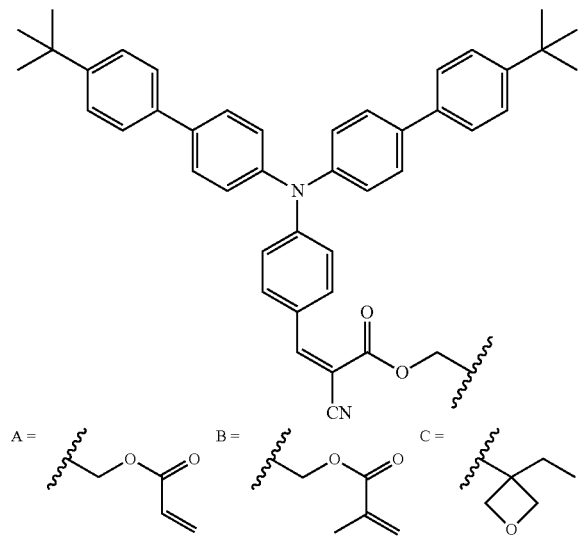

In order to model the polar surroundings and the possible π-π interactions encountered for compounds processed as thin films in multilayer systems, photophysical investigations were performed in toluene.

C.1. Thermal Properties

The use of the compounds of the invention on multilayered electronic or photonic devices requires molecules forming amorphous materials.

Indeed, crystallization or morphologic change of emissive molecules after solution deposition on substrates lead to structural defects that can alter mobility, charge migration and therefore the performances of the final object.

The aim is to show that the compounds of the invention provide amorphous materials, enabling their further use in organic electronics or photonics.

Compounds II-a up to II-d were studied by differential scanning calorimetry between −20° C. and 150° C. in order to determine their glass transition temperature (T$_g$) and/or melting temperature (T$_m$).

Amorphous compounds display glass transition temperature but no melting point (the latter characteristic being proper to the crystalline areas of semi-crystalline or crystalline materials).

The thermal results obtained by DSC are listed in Table 1.

TABLE 1

Phase change temperatures characteristic of the compound of the invention measured by DSC using a 20° C. min$^{-1}$ thermal gradient.

| Compound | T$_g$(° C.) | T$_m$(° C.) |
|---|---|---|
| II-a | 12 | not observed |
| II-b | 28 | not observed |
| II-c | 6.4 | not observed |
| II-d | 1.9 | not observed |
| A | 41 | not observed |
| B | 36 | not observed |
| C | 57 | not observed |

All studied compounds displayed a glass transition temperature T$_g$ between −20° C. and 150° C. with no melting point over this range of temperatures.

Moreover, these results show that compounds II-a up to II-d display a glass transition temperature lower than those of compounds A, B and C. This difference in T$_g$ mainly stems from the nature of the photopolymerizable groups and the existing spacer (i.e. a bulky flexible chain comprising chiral centers in a racemic ratio), between the triphenylamine core and the photopolymerizable group.

In conclusion, the compounds of the invention possess a specific chemical structure responsible for their amorphous character, which allows for their use in the fabrication of organic layers. In particular, the thermal properties of compounds II-a up to II-d impart with enough mobility the molecular chains linked to the acrylate and oxetane groups to favor photo-crosslinking at room temperature.

C.2. UV-Visible Absorption and Emission Properties of Compounds in the Solid State The aim is to show that the presence of photopolymerizable groups on triarylamine derivatives does not perturb the photophysical properties (absorption and emission) of these compound; more particularly, when these compounds are structured as thin films.

The UV-vis absorption and emission properties of compounds II-a up to II-d were studied first in toluene solution and secondly as thin films.

C.2.1. In Toluene Solution

Spacer Influence

Compounds II-a and II-b were dissolved in toluene at a concentration equal to 5·10$^{-5}$ mol/L.

5 Compounds II-a and II-b comprise the same dicyanovinylidene electron-withdrawing group and the same spacer but differ from the nature of the photo-crosslinking group (II-a: acrylate; II-b: oxetane).

Figure 2A:
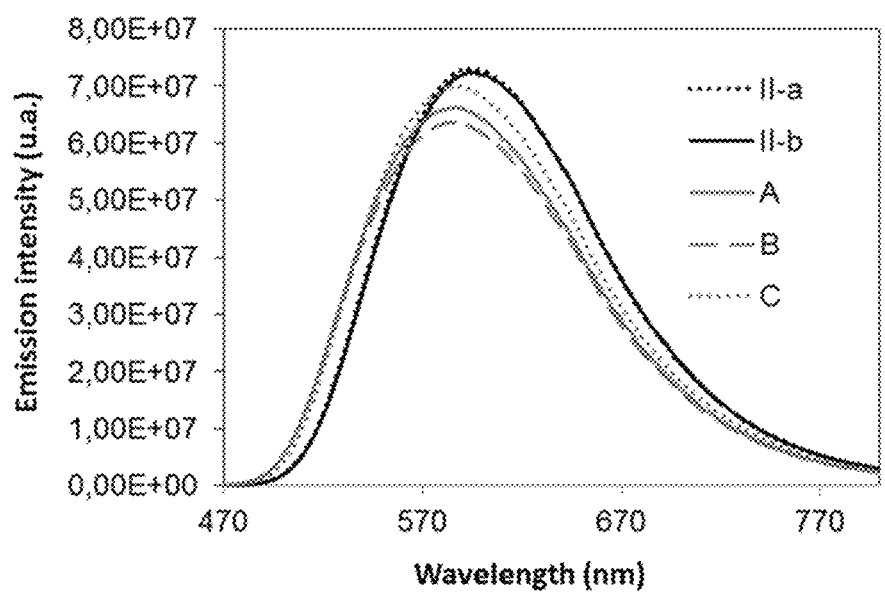
FIG. 2 relates to the UV-vis emission spectra of compounds II-a, II-b, A, B and C (FIG. 2A) or compounds II-a, II-c and II-d (FIG. 2B) in toluene solution.

The results regarding toluene solutions are listed in Table 2 and depicted by FIGS. 1A and 2A.

TABLE 2

Photophysical properties of compounds II-a, II-b, A, B and C in toluene solution. (~5.10$^{-5}$ mol · L$^{-1}$).

| Compound | Absorption band 1 $\lambda_{max}$(abs)/nm [$\varepsilon_{max}$/L · mol$^{-1}$ · cm$^{-1}$] | Absorption band 2 $\lambda_{max}$(abs)/nm [$\varepsilon_{max}$/L · mol$^{-1}$ · cm$^{-1}$] | Emission band$^a$ $\lambda_{max}$(em)/nm | Stokes shift $\Delta\bar{v}$/cm$^{-1}$ | Fluorescence quantum yield$^b$ $\Phi_f$ |
|---|---|---|---|---|---|
| II-a | 450 [30 200] | 324 [19 500] | 595 | 5 410 | 0.29 |
| II-b | 450 [34 000] | 324 [21 800] | 595 | 5 410 | 0.26 |
| A | 445 [34 400] | 325 [22 300] | 589 | 5 490 | 0.31 |
| B | 445 [29 200] | 325 [19 000] | 589 | 5 380 | 0.33 |
| C | 445 [27 700] | 325 [19 500] | 585 | 5 380 | 0.28 |

$^a$Excitation at the absorption maximum.
$^b$Measured from fluorescence standard using coumarin 540A in ethanol ($\Phi_f$ = 0.38).

FIGS. 1A and 2A show the absorption and emission spectra, respectively, of compounds II-a, II-b, A, B and C in toluene solution at a concentration of 5×10$^{-5}$ mol·L$^{-1}$.

All compounds show similar UV-vis absorption spectra with two absorption bands: i) a first band at around 324 nm corresponding to the π-π* transition related to the biphenylamino unit; ii) a second band at around 445 nm corresponding to charge transfer of the triphenylamino core to the electron-withdrawing unit.

For compounds II-a and II-b, i.e. compounds with strong electron-withdrawing group (dicyanovinylidene) and two polymerizable functions separated from the triphenylamino core by spacers, both absorption and emission spectra display a very slight bathochromic shift (namely towards higher wavelengths) compared to those of compounds A, B and C.

Such results show that the photophysical properties of compounds II-a and II-b in toluene solution are not influenced by the existing photopolymerizable groups when the latter are separated from the triarylamino core by a spacer. Especially, the presence of a flexible hindered chain comprising a chiral center between the triphenylamino core and the photopolymerizable group allows avoiding the electronic coupling of the photopolymerizable group and the triarylamino core.

Influence of the Electron-Withdrawing Group

Compounds II-a, II-c and II-d were dissolved in toluene at a concentration of 5×10$^5$ mol·L$^1$.

All compounds II-a, II-c and II-d comprise two acrylate functions separated from the triarylamino core by identical spacers but present distinct electron-withdrawing groups.

Figure 1B:
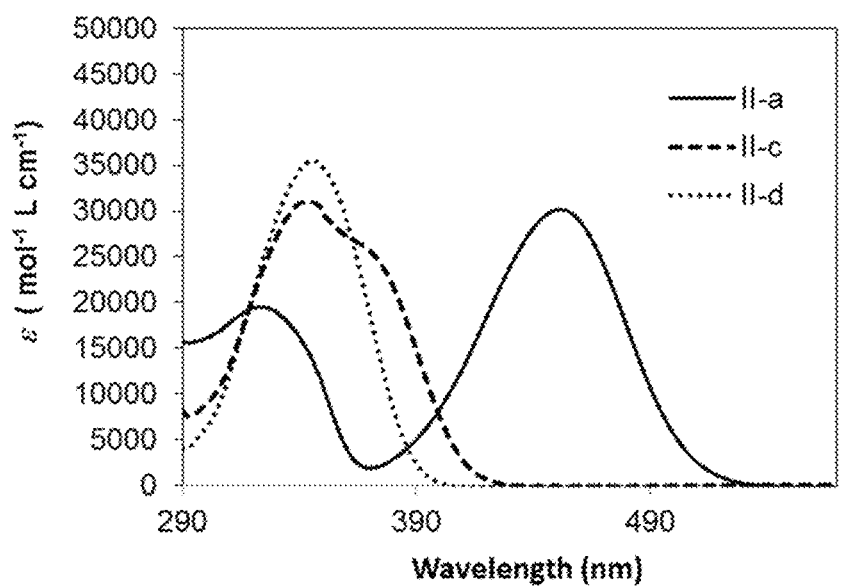
Figure 2B:
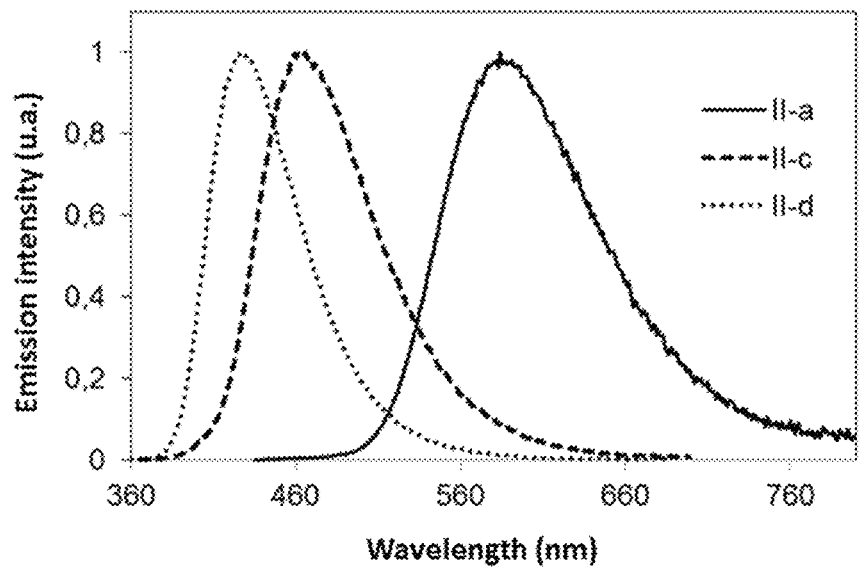

The results obtained in toluene solution are listed in Table 3 and depicted by FIGS. 1B and 2B.

TABLE 3

Photo-physical properties of compounds II-a, II-c and II-d, in toluene solution (~5.10$^{-5}$ mol · L$^{-1}$).

| Compound | Absorption band 1 $\lambda_{max}$(abs)/nm [$\varepsilon_{max}$/L · mol$^{-1}$ · cm$^{-1}$] | Absorption band 2 $\lambda_{max}$(abs)/nm [$\varepsilon_{max}$/L · mol$^{-1}$ · cm$^{-1}$] | Emission band$^a$ $\lambda_{max}$(cm)/nm | Stokes shift $\Delta\bar{v}$/cm$^{-1}$ | Fluorescence quantum yield$^a$ $\Phi_f$ |
|---|---|---|---|---|---|
| II-a | 452 [30 200] | 323 [19 500] | 585 | 5 030 | 0.29 |
| II-c | 370 [25 900] | 345 | 465 | 5 520 | 0.37 |
| II-d | 346 [35 500] | — | 428 | 5540 | 0.28 |

$^a$Excitation at the absorption maximum.
$^b$Measured from fluorescence standard using coumarin 540A in ethanol as reference ($\Phi_f$ = 0.38).

The results show very distinct absorption and emission spectra for compounds II-a, II-c and II-d due to increasing charge transfer for compound II-d to compound II-c and, being maximum for compound II-a. Such discrepancy is more pronounced for emission compared to absorption owing to enhanced dipole moment in the excited state. Various compounds, emitting in distinct spectral ranges (blue, green-blue, red-orange), can be obtained upon mere change of the electron-withdrawing group (Z) without modifying the rest of the molecular backbone. All compounds are strongly emissive with a fluorescence quantum yield $\Phi_f$, largely superior to 0.1. For all compounds, the emission spectra are strongly shifted from the absorption ones, with a large Stokes shift (>5000 cm$^1$), featuring nuclear reorganization at the excited state. Large Stokes shift value is typical of weak reabsorption of the light emitted by the surrounding molecules and warrants efficient emission in the solid state as thin films, which is a mandatory pre-requisite for the fabrication of performing electroluminescent devices.

C.2.2. As Thin Films

Spacer Influence

Various 130 nm-thick films were fabricated out of neat compounds II-a, II-b, A, B or C following the above mentioned procedure.

The aim is to demonstrate that the photophysical properties of these compounds, be they processed as neat films or dissolved in toluene solution, do not change significantly change.

Figure 3A:
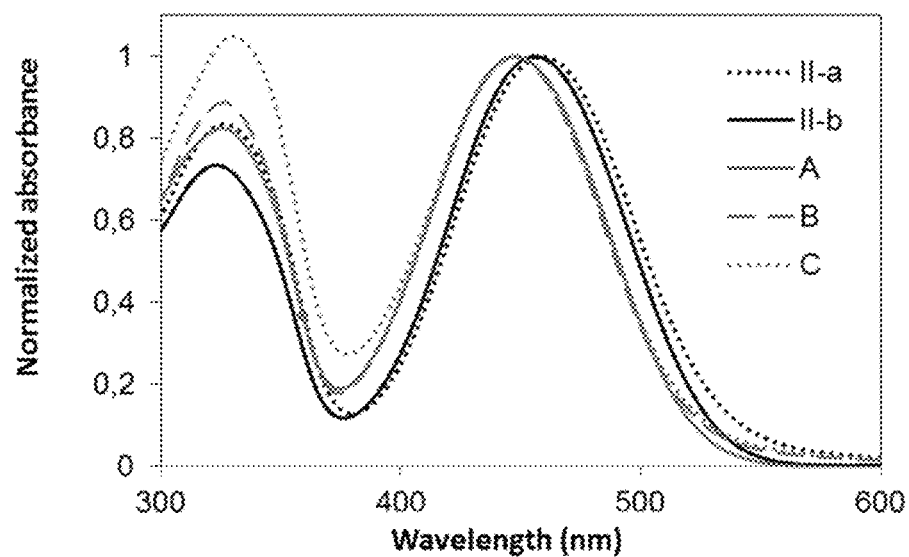
FIG. 3 relates to the absorption spectra of compounds II-a, II-b, A, B and C (FIG. 3A) or compounds II-a, II-c and II-d (FIG. 3B) processed as thin films.
Figure 4A:
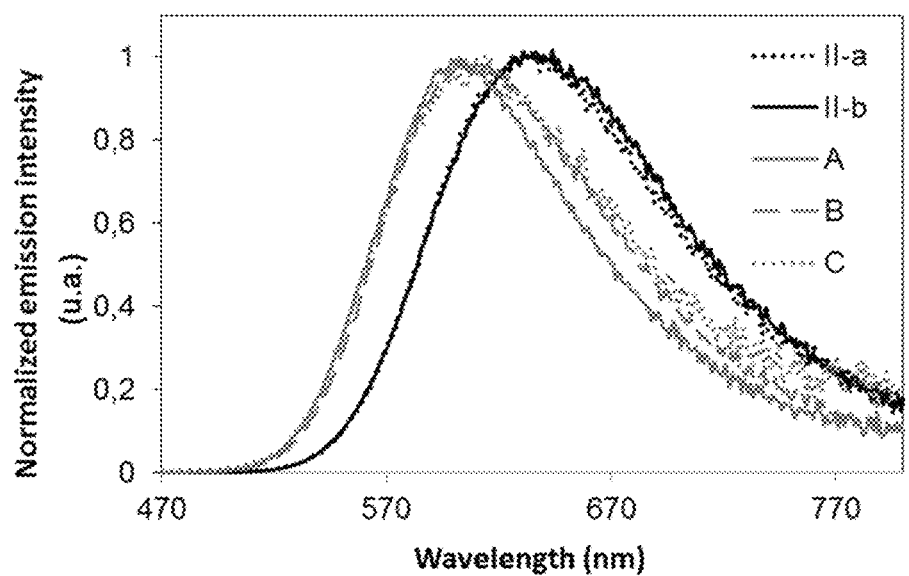
FIG. 4 relates to the emission spectra of compounds II-a, II-b, A, B and C (FIG. 4A) or compounds II-a, II-c and II-d (FIG. 4B) processed as thin films.

The results obtained in toluene solution are listed in Table 4 and depicted by FIGS. 3A and 4A.

TABLE 4

Photo-physical properties of compounds II-a, II-b, A, B and C processed as thin films.

| Compound | Absorption band 1 $\lambda_{max}$(abs)/nm | Absorption band 2 $\lambda_{max}$(abs)/nm | Emission band[a] $\lambda_{max}$(em)/nm | Stokes shift $\Delta\bar{\nu}/cm^{-1}$ |
|---|---|---|---|---|
| II-a | 459 | 326 | 635 | 6 040 |
| II-b | 459 | 326 | 635 | 6 040 |
| A | 448 | 326 | 607 | 5 850 |
| B | 448 | 326 | 601 | 5 680 |
| C | 448 | 326 | 607 | 5 850 |

[a]Excitation performed at the absorption maximum.

The results demonstrate the absence of change in the absorption spectra when going from toluene solution to thin films (identical maximum absorption wavelengths for compounds II-a and II-a on one hand and A, B, and C on the other hand; large Stokes shift).

As for the emission spectra, a significant 40 nm bathochromic Stokes shift is however noticed when compounds II-a et II-b are processed as thin films. These results show more polar surroundings within thin films fabricated out of II-a et II-b, enabling better stabilization of the charge transfer excited state of compounds II-a and II-b compared to compounds A, B and C.

In conclusion, these results show that the formation of thin films made out of the compounds of the invention does not alter their photo-physical properties.

Influence of the electron-withdrawing group Various 130 nm-thick films have been fabricated out of neat II-a, II-c, and II-d following the above mentioned procedure.

Figure 3B:
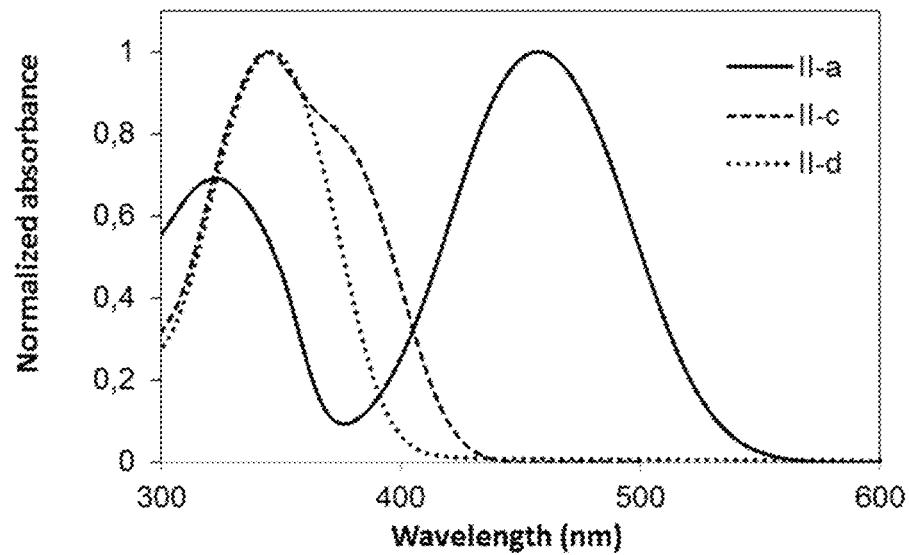
Figure 4B:
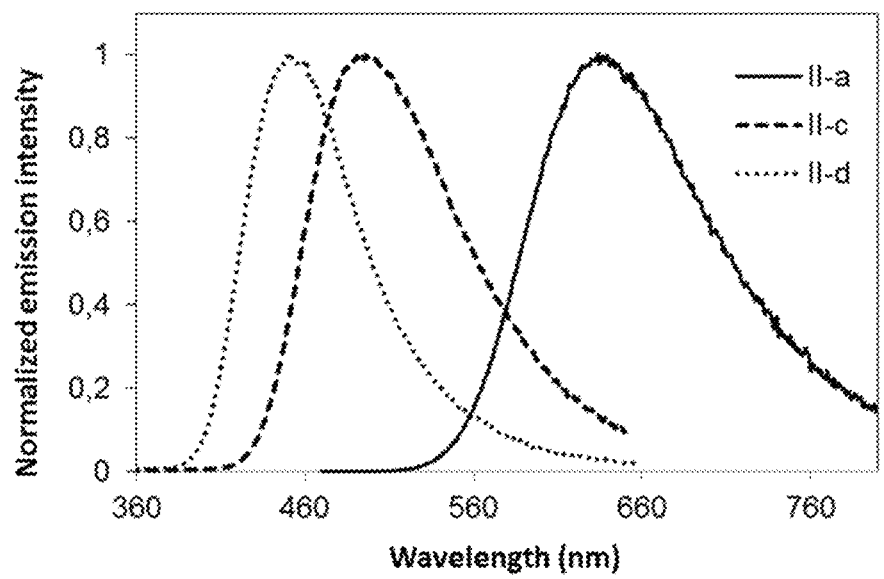

The results obtained in toluene solution are listed in Table 5 and depicted by FIGS. 3B and 4B.

TABLE 5

Photo-physical properties of compounds II-a, II-b, II-c processed as thin films.

| Compound | Absorption band 1 $\lambda_{max}$(abs)/nm | Absorption band 2 $\lambda_{max}$(abs)/nm | Emission band[a] $\lambda_{max}$(em)/nm | Stokes shift $\Delta\bar{\nu}/cm^{-1}$ |
|---|---|---|---|---|
| II-a | 458 | 323 | 635 | 6 090 |
| II-c | 370 | 345 | 496 | 6 870 |
| II-d | 346 | — | 450 | 6 680 |

[a]Excitation performed at the absorption maximum.

The results demonstrate that compounds processed as thin films display similar absorption properties as those in toluene solution while their emission signals are clearly shifted to lower energy, with emission centered in the blue, the green and the red regions. These photo-physical characteristics allows envisaging the mixture of three compounds in such carefully calculated ratios that white light emission can be generated.

D. Studies of Electrochemical Properties

The aim is to demonstrate that the compounds of the invention behave more as electron-rather than as hole-transporting materials.

The electrochemical measurements of the redox potentials are performed using cyclic voltametry, using a three-electrode setup. The working electrode and counter electrode are platinum electrodes while the reference electrode is a AgCl/Ag pseudo-reference electrode. Potentials are referred to the standard redox potential of ferricinium/ferrocene couple $E^0(Fc^+/Fc)$ equal to 0.64 V vs ENH. A 0.1 $V \cdot s^{-1}$ scan rate was selected with no possibility to make the second oxidation wave reversible at higher scan rate.

D.1. Electrochemical Properties of Compounds A, B and C

Compounds A, B and C comprise no spacer. Conversely, they incorporate electron-withdrawing groups with distinct photopolymerizable functions.

Compounds A, B and C comprise the same chromophore, responsible for the first electrochemical oxidation.

Figure 5A:
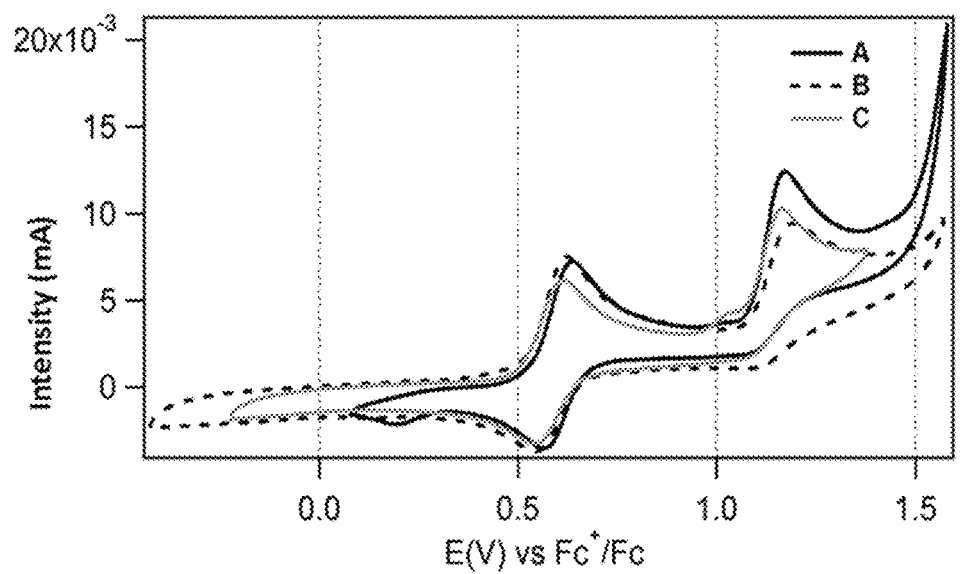
FIG. 5 relates to cyclic voltammograms of compounds A, B and C (FIG. 5A) or compounds II-a, II-c and II-d (FIG. 5B), recorded in 10-3 mol·L−1 acetonitrile (support electrolyte: nBu4NPF6 (0.1 mol·L−1); scan rate: 0.1 V·s−1).

The results obtained from cyclic voltammetry are depicted by FIG. 5A.

Oxidation first regards the triphenylamino core and is characterized by a quasi-reversible wave, centered at a half-wave potential almost identical at 0.60-0.61 V for all compounds A, B and C. Oxidation potentials of the second oxidation wave appear at slightly higher voltage. Yet, this shift is not significant due to the non-complete reversibility of the oxidation process.

These results show that the values of oxidation potential are close to those in literature, hence compounds A, B and C are expected to display higher electron-transporting capability than hole-transporting one.

D.2. Electrochemical Properties of Compounds II-a, II-c and II-d

Figure 5B:
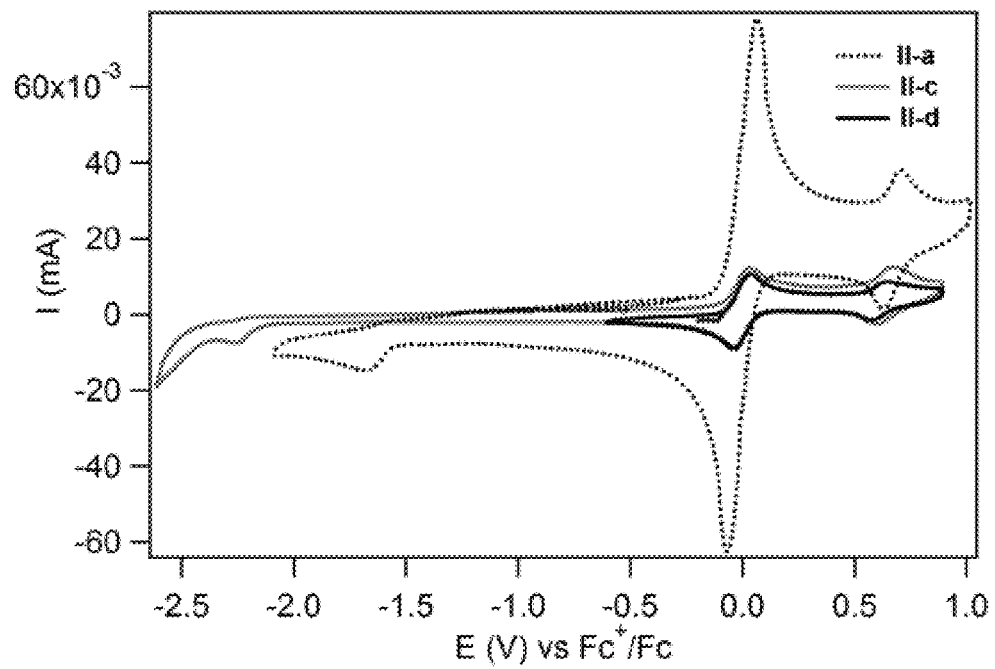

Compounds II-a, II-c and II-d comprise identical spacers and distinct electron-withdrawing groups. The results obtained from cyclic voltammetry are reported in FIG. 5B.

These experiments evidence two mono-electron oxidation waves corresponding to the successive oxidation of the triphenylamino core into triphenylammonium radical cation and the triphenylammonium cation.

These results show that the electrochemical properties are independent of the photopolymerizable groups in the same as the photophysical properties were, which confirms the absence of π-conjugation between the emissive moieties and photoreactive moieties. Such decoupling accounts for the acrylate photoreactivity observed for compounds A, B and C. The obtained values show that the radiative π-conjugated system wherein the hole-electron pair is supposed to recombine behaves more like an electron carrier rather than a hole carrier. Such characteristics will rule the stacks further fabricated and be essential to ensure efficient charge transport through the emissive layer.

E. Fabrication of Insoluble Emissive Layers

The aim of these experiments is to demonstrate that the compounds of the invention enable the fabrication of insoluble emissive layers upon photopolymerization.

The aim also is to show that the reaction conditions of photopolymerization do not alter the photophysical properties of the compounds constituting the insoluble organic layer after reaction.

E.1. Synthesis of an Insoluble Emissive Organic Layer

Various compositions comprising compounds II-a or II-b (1 wt. %) and diphenyl(2,4,6-trimethylbenzoyl)phosphine oxide as a photoinitiator (2 to 5 mol. % relative to compound II-a or II-b) have been prepared in chloroform.

One of these compositions (with compound II-a) was spin-cast on a glass substrate. To such purpose, the photopolymerizable composition was pre-filtered using a PTFE filter (Millex, 0.45 μm), placed on a 1 mL glass syringe. The spin-coating and drying steps were carried out at a rotation speed of 1000 rpm for 60 s and at a spin acceleration of 500 rpm/min. A thin film is obtained.

Then, crosslinking of the film deposited on the substrate was performed through photopolymerization at a 365 nm irradiation wavelength.

Photoconversion

Progress of the photopolymerization of compound II-a was monitored using infrared spectroscopy. The photopolymerizable solution was deposited on a KBr plate and irradiated in situ at 365 nm to initiate the photopolymerization reaction. Infrared spectroscopy monitoring was performed at 810 $cm^{-1}$ which corresponds to the out-of-plane C—H bending mode of the photopolymerizable acrylate moiety. The band of the stretching mode of the ester carbonyl groups at 1750 $cm^{-1}$ served as an internal reference.

Figure 6:
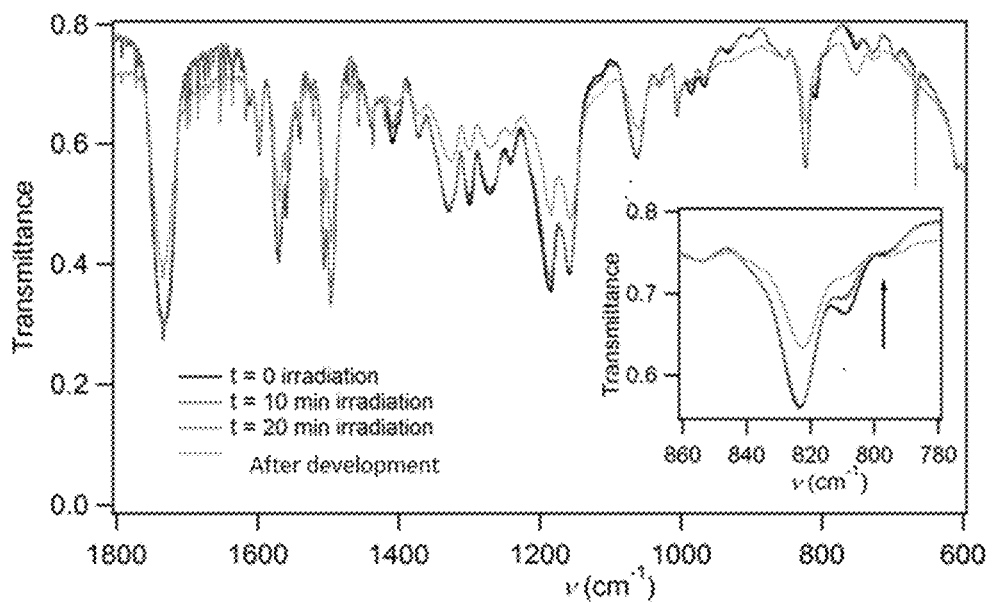
FIG. 6 relates to the evolution in infrared absorption spectroscopy of the vibration band at 810 cm−1 (characteristics of photopolymerizable acrylate functions) during the polymerization reaction of compounds II-a.

FIG. 6 depicts the evolution of the vibration band resonating ay 810 $cm^{-1}$.

In the course of irradiation, the band, characteristic of the polymerizable functions (at 810 $cm^{-1}$) significantly decreases. This result shows that the employed reaction conditions enable photopolymerization of compound II-a.

The photoconversion yield of compound II-a after irradiation is about 53%. After development, the percentage of crosslinked monomers compared to non-photocrosslinked ones is about 92%, which corresponds to a high yield of crosslinking of the emissive organic layer.

Photopolymerization Efficiency

In order to perform photopolymerization of the organic film without degrading its emissive properties, the irradiation power and duration were investigated.

The compounds of the invention were dissolved in the presence of a photoinitiator in an organic solvent, spin-cast as thin films on a substrate and further photoplymerized upon irradiation at 365 nm.

Figure 7A:
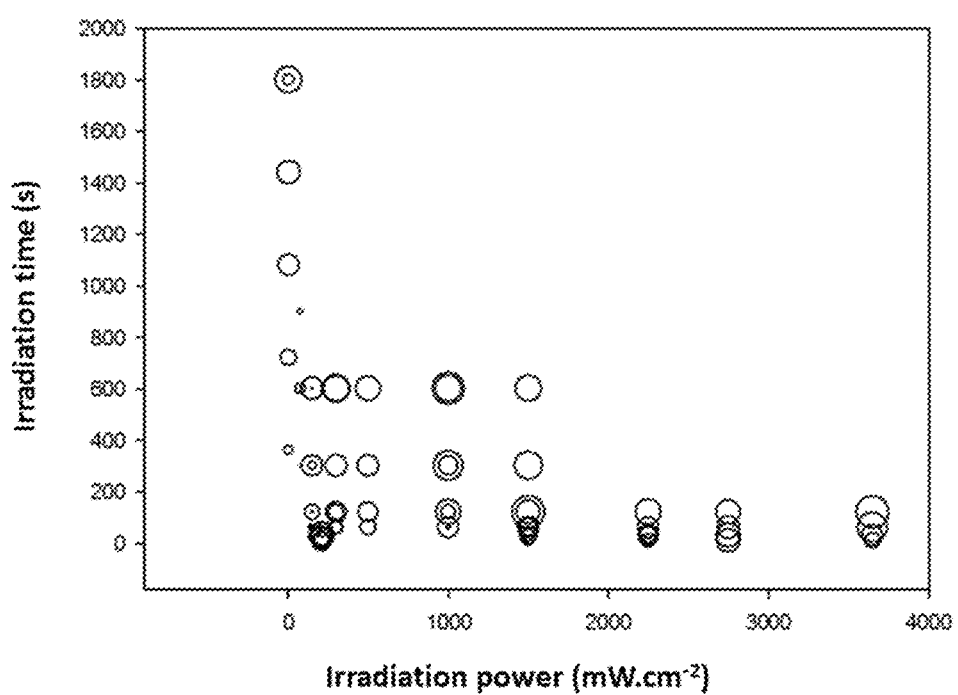
FIG. 7 relates to the evolution of the maximum absorbance (FIG. 7A) and fluorescence signal intensity (FIG. 7B) of developed organic layers at given irradiation power and irradiation.
Figure 7B:
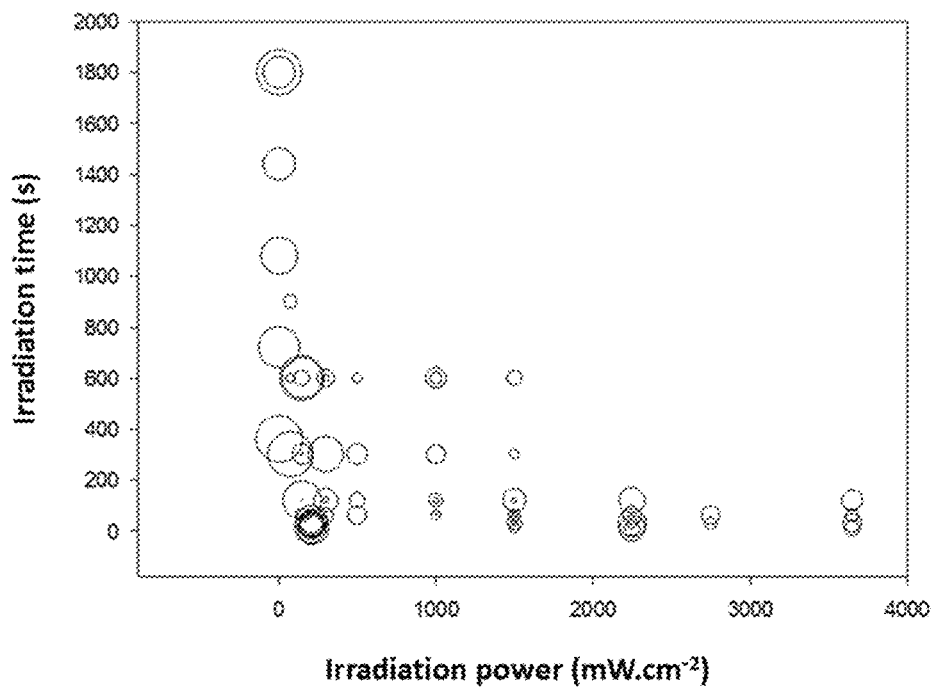

The absorption and fluorescence responses of various organic layers were then studied. FIGS. 7A and 7B display the efficiency of the photopolymerization process (in absorption and fluorescence respectively), as a function of the irradiation power and duration.

The size of the circles drawn on each graph represents the absorbance and emission signals of the photopolymerized organic layer compared to those of the organic layer before photopolymerization.

The larger the circle, the higher the absorbance and the fluorescence.

The results show that:
  for low irradiation power and short irradiation time, absorbance is weak;
  for high irradiation power and long irradiation time, absorbance is high and fluorescence intensity is weak;
  for low irradiation power and long irradiation time, both the absorbance and fluorescence intensity are larger.

In conclusion, these experiments show that low-power irradiation for long time conducts to insoluble organic layer while keeping good emissive properties.

E.2. Characterizations of the Insoluble Organic Layer

Thickness of the Insoluble Organic Layer

After removing the non-photopolymerizable compounds by washing with chloroform several times, an insoluble emissive organic layer is obtained with a thickness of around 130 nm (measured using a Dektak Veeco 8 mechanical profilometer).

Figure 8:
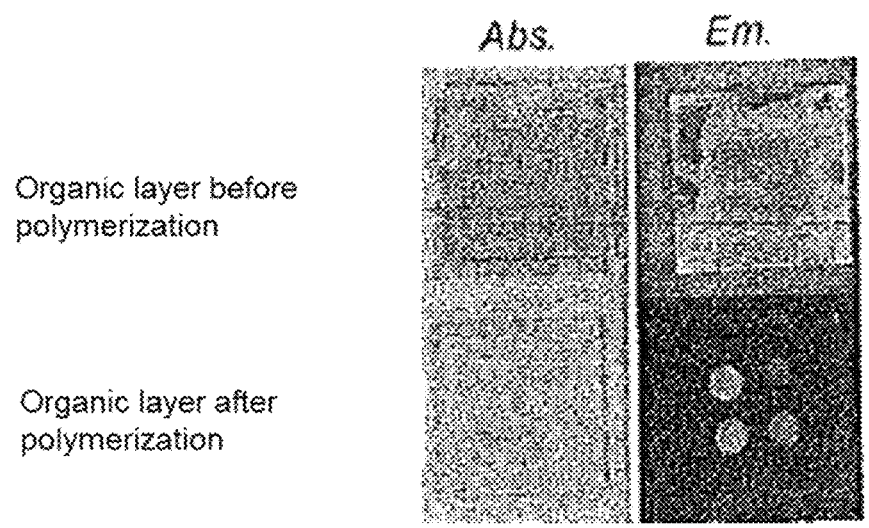
FIG. 8 represents the picture in transmission (Abs) and emission (EM) of emissive organic thin films before and after development.

FIG. 8 represents the picture in transmission (Abs) and emission (EM) of photo-irradiated organic thin layers obtained by spin-coating a solution containing compound II-a, before and after development with organic solvents.

These results show efficient photo-crosslinking in the irradiated areas since matter remains after development. They also prove that the film keeps its emissive properties since the photo-crosslinked areas keep emitting. They evidence that prolonged irradiation leads to superior photo-crosslinking, hence a higher thickness for the photo-crosslinked material and a greater emission (irradiation time increasing clockwise according to 1 min., 3 min., 5 min., 10 min. at a constant 30 mW·$cm^{-2}$ power). Prolonged irradiation however leads to more extensive photodegradation since the brightest area after development (top left) also matches the area that emits the less before development by comparison with the rest of the non-irradiated sample. A compromise in terms of energy dose (product of irradiation power with irradiation time) prompts to adopt an energy dose comprised between 0 and 100 J·$cm^{-2}$; preferably less than 20 J·$cm^{-2}$; preferably less than 10 J·$cm^{-2}$; preferably less than 6 J·$cm^{-2}$.

Topographic Analyses

The aim is to obtain insoluble emissive organic layers displaying no structural defects.

Any structural defect of the emissive organic later impairs the photophysical properties of the latter. Yet, it is known to the person skilled in the art that photo-crosslinking leads after reaction to shrinking of the organic thin layers. This phenomenon mostly creates cracks or microreliefs within the photopolymerized material; the material can no longer be used in multilayered electronic or photonic devices. Therefore, polymerization conditions strongly influenced the structure of organic layers after polymerization, and thereby their emissive properties.

In order to control the absence of defect within the resulting organic layers and control the efficiency of the polymerization conditions, topographic analyses were performed using a mechanical profilometer and atomic force microscope.

Comparison between two organic layers obtained following distinct polymerization conditions was made using: 1) high irradiation power for a short irradiation time; or 2) low irradiation power for a longer irradiation time.

Figure 9A:
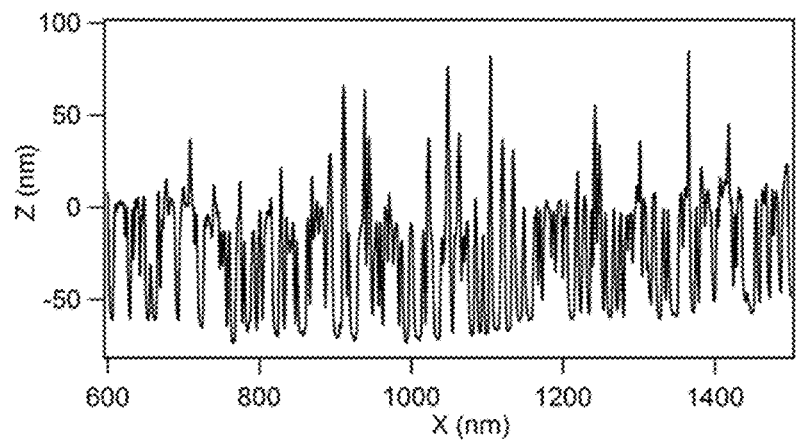
(FIG. 9A) or at an irradiation power of 30 mW·cm−2 for 5 min.
Figure 9B:
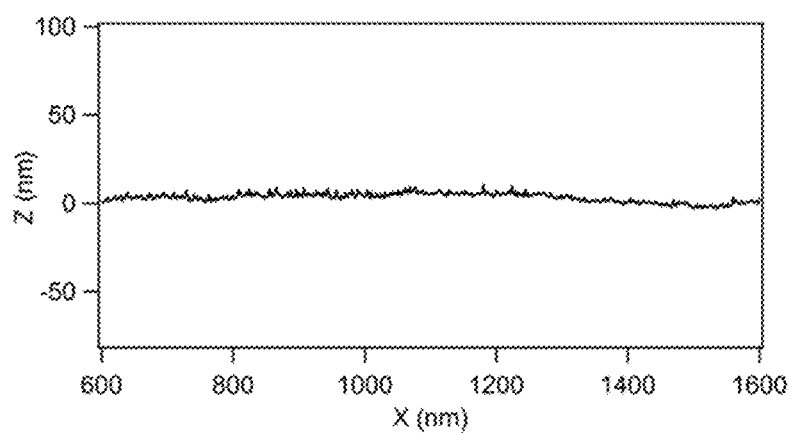
(FIG. 9B).

FIGS. 9A and 9B show the topographic results regarding both organic layers after polymerization.

FIG. 9A clearly shows that polymerization conditions based on high irradiation power (450 mW·$cm^{-2}$ for 1 min.) leads to a heterogeneous surface with micro reliefs and defects.

FIG. 9B shows that for milder polymerization conditions based (30 mW·cm$^{-2}$ for 5 min.), the surface of the insoluble organic layer surface is homogeneous and displays neither defects, nor micro reliefs.

Optimized irradiation conditions (irradiation power of 3.5 mW·cm$^{-2}$ for 30 min.) have been implemented and led to very smooth surfaces after polymerization, with root mean square roughness of 0.7 nm, very close to that of the surface before polymerization.

In conclusion, these results demonstrate that optimized conditions of the photopolymerization of the compounds of the invention enable the fabrication of insoluble emissive organic layers with controlled thickness and devoid of structural defects, after polymerization. The compounds of the invention can be used as precursors of emissive layers for applications in organic electronics and photonics.

F. Fabrication of Photo-Crosslinked Fluorescent Organic Nanoparticles (FONs)

The aim of these experiments is to demonstrate that the compounds of the invention allow providing insoluble photo-crosslinked fluorescent organic nanoparticles.

F.1. Nanoparticule Fabrication

F.1.1. Bulk Fabrication

Monocomponent Nanoparticles

A solution of photopolymerizable compound II-a or II-c (1 mg) and TPO photoinitiator (10 mol. % with respect to the dye concentration) was prepared in THF (1 mL). 50 µL of this solution were quickly added under stirring into Millipore water (2.5 mL) to form bright spots, visible under fluorescence microscope using an oil-immersion objective (magnification 60×, numerical aperture 1.43).

Bicomponent Nanoparticles

Method A.

A mixture of compounds II-a and II-c (1 mg of each) and TPO (10 mol. %) was prepared in THF (1 mL). Nanoprecipitation was performed using the same protocol as that previously described for monocomponent nanoparticles, and yielded nanoparticles (the total amount of II-a and II-c).

Method B. Two distinct solutions of compound II-a or compound II-c (1 mg) containing each TPO (10 mol. %) were prepared in THF (1 mL). Nanoprecipitation was performed using first the solution of compound II-a following the same protocol as that previously described for monocomponent nanoparticles. To the solution of II-a nanoparticles were added 50 µL of solution of compound II-c. In this way, a solution of fluorescent organic nanoparticles II-a and II-c was formed.

F.1.2. Microfluidic Fabrication

A microfluidic setup, made of colinear tubings, an injection needle, and three syringe pumps, could also be used to fabricate photopolymerized FONs.

A first glass syringe (5 mL) was filled with THF solution of one or two fluorescent dyes (0.1% wt.) and the flow was fixed at 10 µL·min$^{-1}$. A second plastic syringe (5 mL) was filled with Millipore water and the flow was fixed at 40 µL·min$^{-1}$. Finally, a third glass syringe (10 mL) was filled with Fomblin® and the flow was fixed at 100 µL·min$^{-1}$.

Both water and THF solution were mixed inside droplets that formed inside the microfluidic setup. Each droplet was separated by perfluorinated oil (Fomblin® type) droplets so that micrometric volumes of nanoprecipitation could be generated. The entire flow of fluids was recuperated and the aqueous layer was separated from the Fomblin® layer after short stirring using a vortex.

F.2. Nanoparticle Photopolymerization

Photopolymerization was performed only with nanoparticles fabricated in bulk solution and incorporated a single component or two components following method A or method B.

Irradiation was used to induce cross-linking either during the nanoprecipitation step or once the nanoparticles have been fabricated. Careful deoxygenation of water before mixing or after forming nanoparticles was carried out using gentle argon bubbling during 2 min. The solution was irradiated for 30 s using a UV lamp equipped (maximum power) with a 365 narrow bandpass filter and a quartz light guide, while maintaining argon bubbling.

F.3. Characterizations

F.3.1. Fluorescence Microscopy

The aim is to study the fluorescent properties of nanoparticles obtained from the compounds of the invention.

For this purpose:
- first, addition of THF to a drop of non-irradiated solution of nanoparticles (i.e. no-photo-crosslinked nanoparticles) was carried out. This experiment led to the dissolution of nanoparticles into individual molecules featured by a considerable decrease in fluorescence and a loss of the spot-like emission signal;
- then, THF was added to a solution of irradiated solution of nanoparticles (i.e. photo-crosslinked nanoparticles). In this case, no particular drop of the emission was noted while the spot-like character emission signal remains.

These results show that individual molecules actually emit weakly or less intensively than in the solid state and as nanoparticles, which also provides homogeneous emission throughout the solution.

F.3.2. Photophysical Properties

The aim is to study the influence of the irradiation on the photophysical properties of nanoparticles.

The emission spectra for FONs made of compound II-a were measured before and after irradiation.

The emission spectra for FONs made of compound II-a were found identical whatever the irradiation step order (once the nanoparticles have been generated (post irradiation) or during nanoprecipitation (pre-irradiation).

Figure 10A:
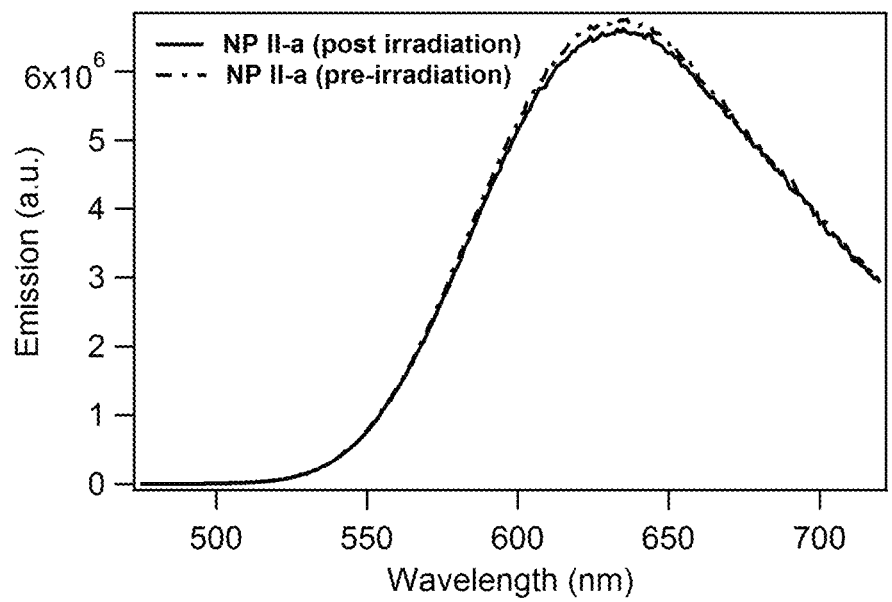
FIG. 10 relates to the UV-vis emission spectra of nanoparticles comprising compounds II-a (FIG. 10A) and the UV-vis emission of nanoparticles comprising a mixture of compounds II-a and II-c (FIG. 10B).

This results shows that nanoprecipitation (usually on the µs to ms time range) is not influenced by irradiation (FIG. 10A).

After photoirradiation, FONs solution (Nanoparticles (II-a+II-c)) made of co-precipitated compounds II-a (red-emissive) and II-c (green emissive) was compared to a FON solution made of successive precipitation of compound II-a (red-emissive) and compound II-c (green-emissive) (NP II-a+NP II-c).

Figure 10B:
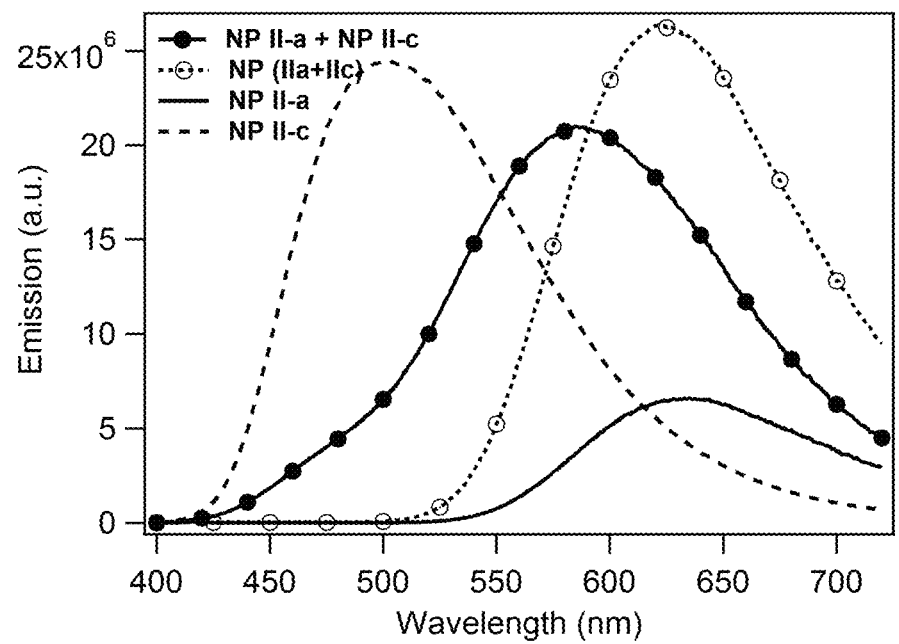

The results are shown FIG. 10B and Table 6.

TABLE 6

Emission maximum wavelength of photo-crosslinked FON solutions made of monocomponent dyes (II-a or II-c), bicomponent dyes (coprecipitated NP (II-a + II-c) or successively precipitated NP II-a + NP II-c).

| FON | NP (II-a) | NP (II-c) | NP (II-a + II-c) | NP II-a + NP-II-c |
|---|---|---|---|---|
| ($\lambda^{max}$(em) (nm) | 633 | 500 | 623 | 585 |

The emission spectra of both solutions largely differ:
- the fluorescent organic nanoparticles (II-a+II-c) solution display emission centered at 623 nm, close to the emission maximum of FONs made exclusively of compound II-a ($\lambda_{max}$(em.)=633 nm), which proves efficient energy transfer from the green emitter to the red emitter (Table 6);
- on the contrary, successive precipitation of compound II-a and then compound II-c in the same solution yields an emission signal with both green and red components.

These results evidence the possibility of fabricating photo-crosslinked fluorescent nanoparticles with distinct colors by choosing the nanoparticle fabrication method and adjusting the dye composition as a function of the stock solution concentration, the emission spectrum and the quantum yield of each involved species.

F.3.3. Structural Properties

Figure 11A:
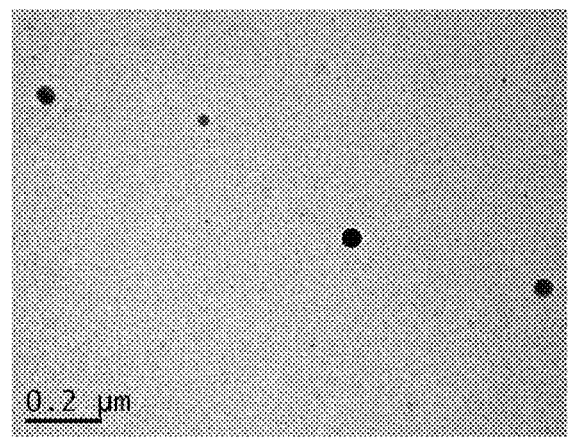
FIG. 11 relates to TEM images of photo-crosslinked fluorescent nanoparticles made of photopolymerized compounds II-a (FIG. 11A) or II-c (FIG. 11B).
Figure 11B:
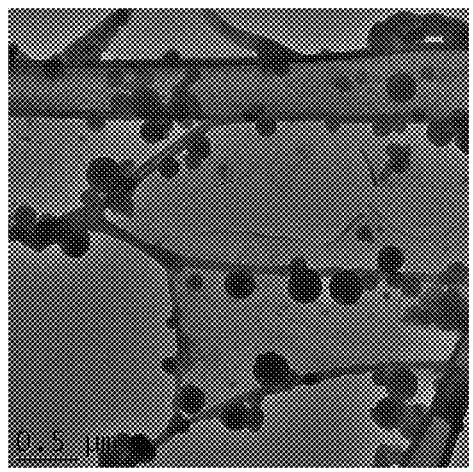

Transmission electron microscopy imaging of photo-crosslinked nanoparticles made of photopolymerized dye II-a (FIG. 11A) or II-c dyes have been recorded (FIG. 11B).

The samples were deposited on TEM copper grids coated with carbon thin films and lacey carbon copper grids respectively.

The mean average size (less than 100 nm or less than 200 nm) depends on the studied compound and the reaction conditions (solvent composition, concentration of the dye stock solution, irradiation time).

The invention claimed is:

1. A photopolymerizable emissive compound of general formula (I):

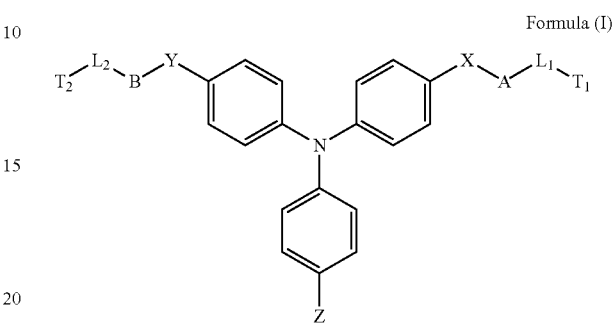

Formula (I)

wherein X and Y each independently represent an aryl or heteroaryl;
A and B each independently represent a chiral center;
$L_1$ and $L_2$ each independently represent an alkyl group comprising 1 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group;
$T_1$ and $T_2$ each independently represent a photopolymerizable group selected from at least one acryloyl, alkylacryloyl, oxetane, alkyloxetane, styryl, allyl, acrylamide, methacrylamide or cinnamate;
Z represents an electron-withdrawing group.

2. A photo-crosslinkable emissive compound of general formula (II-a), (II-b), (II-c) or (II-d) according to claim 1:

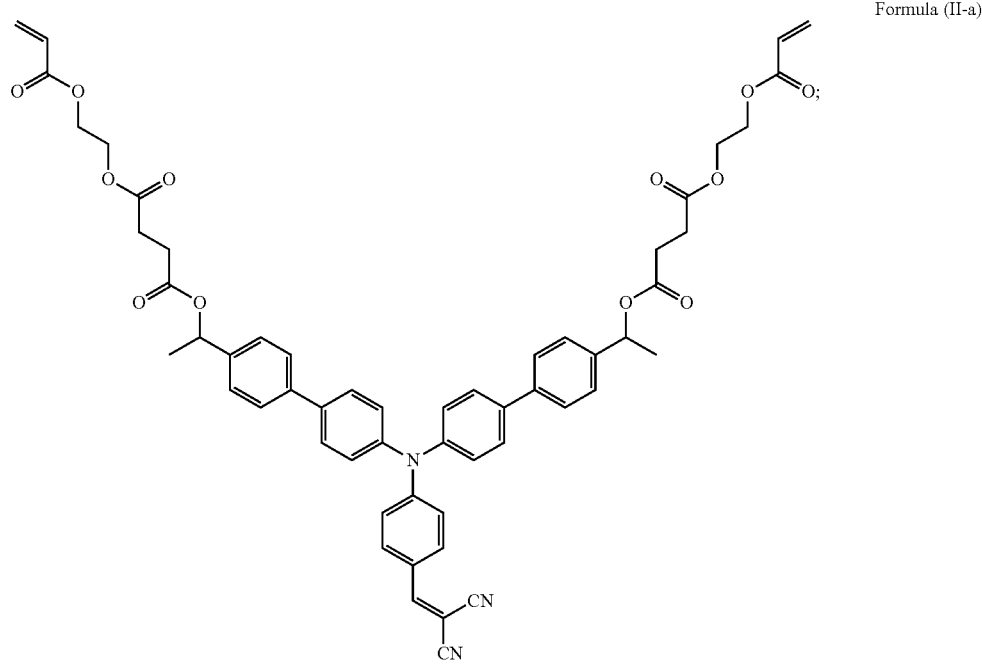

Formula (II-a)

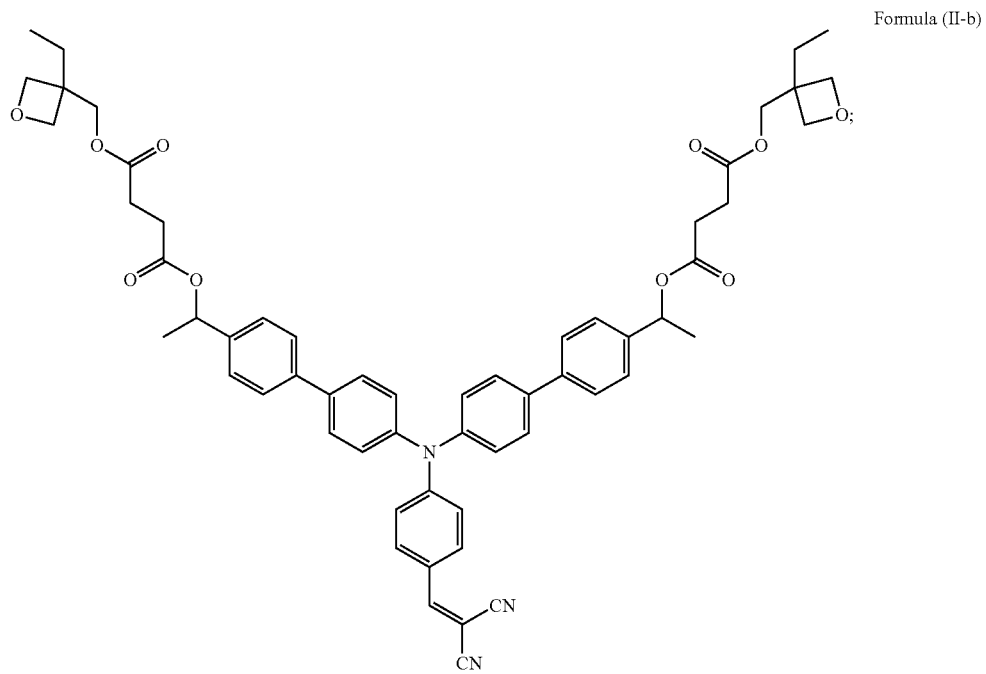
Formula (II-b)
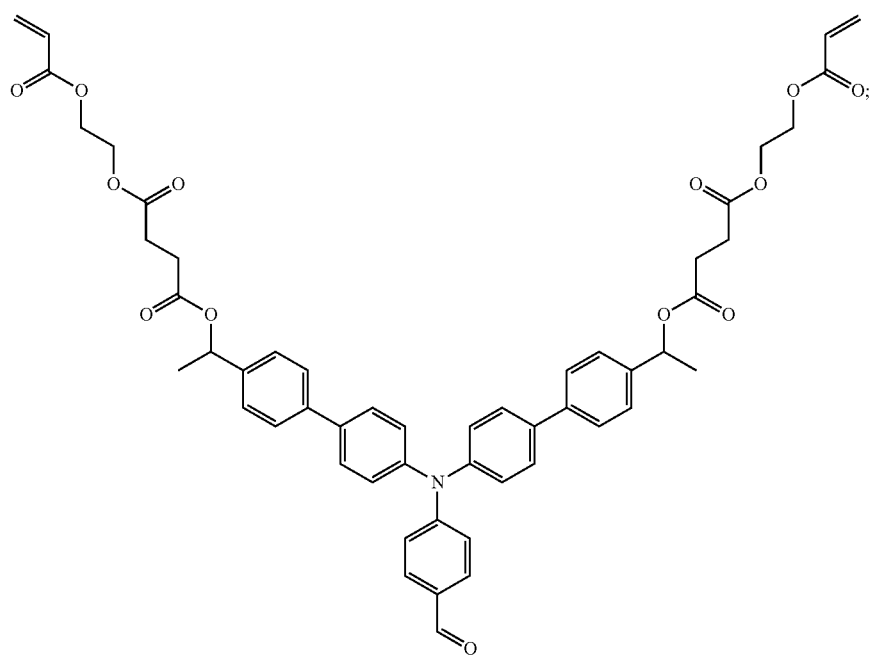
Formula (II-c)

Formula (II-d)

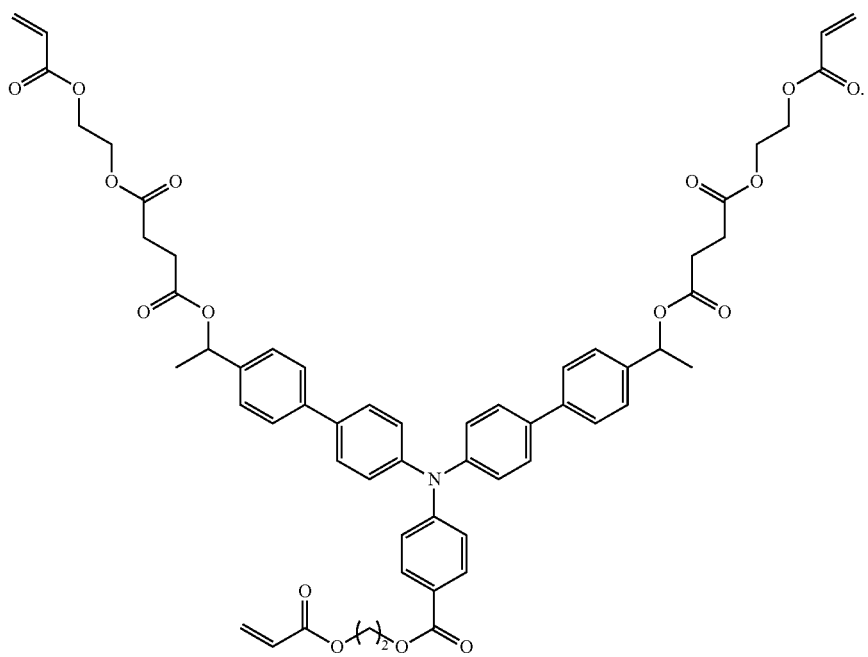

3. An intermediate compound of general formula:

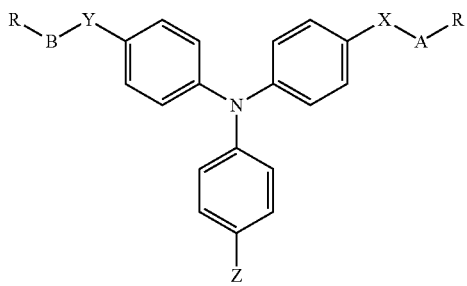

wherein X and Y each independently represent an aryl or heteroaryl;

R represents a —OH or —OTBDMS group;

A and B each independently represent a chiral center; and

Z represents an electron-withdrawing group.

4. A composition comprising at least one compound according to claim 1, an initiator and an organic solvent.

5. A kit comprising a first compartment comprising at least one compound according to claim 1, and an organic solvent, and a second compartment comprising the photoinitiator.

6. A method for manufacturing a compound according to claim 1, comprising:

(i) synthesizing an intermediate compound of general formula (III-2) comprising an aldehyde group:

Compound (III-2)

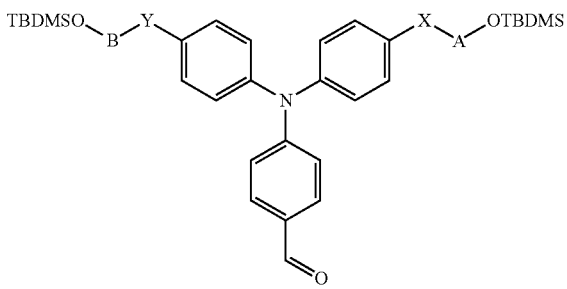

wherein A, B, X and Y are defined as in claim 1, obtained by the reaction of the 4-di(4-bromophenyl)aminobenzaldehyde with the compound of formula (III-1):

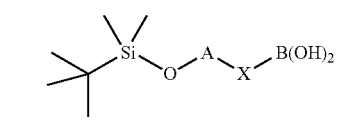

also noted as

TBDMSO—A—X—B(OH)₂ wherein A represents a chiral center; and X represents an aryl or heteroaryl;

(ii) a deprotection reaction;

(iii) in the case where Z of the compound according to claim 1 is not an aldehyde group, modifying the aldehyde group of the intermediate compound (III-2) into another electron-withdrawing group Z allowing the provision of intermediate compound of formula (III-3bis):

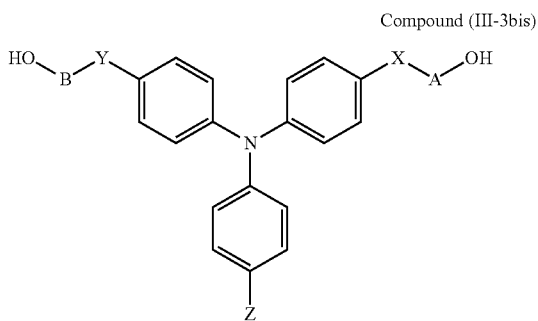

Compound (III-3bis)

wherein A, B, X and Y are defined as in claim 1, and Z represents an electron-withdrawing group;

(iv) and, modifying the compound obtained in (ii) in the case where Z of the compound according to claim 1 is an aldehyde group, or in (iii) in the case where Z of the compound according to claim 1 is not an aldehyde group, allowing for the introduction of spacers L comprising at least one photopolymerizable group T.

7. A method for manufacturing a substrate coated with a thin, amorphous, emissive, photo-crosslinkable and non-doped small molecule-based film, comprising the following steps:
   a) providing a composition comprising at least one compound of general formula according to claim 1, a solvent and a photoinitiator;
   b) depositing the composition obtained in a) onto a substrate.

8. A method for manufacturing a photo-crosslinked emissive organic layer or a photo-crosslinked emissive multilayer system comprising the following steps:
   a') implementing the method of manufacturing a substrate coated with a photo-crosslinkable emissive film according to claim 7; then b') the photopolymerization of said film;
   c') optionally, repeating steps a') and b') resulting in an insoluble emissive multilayer device.

9. A composition comprising at least one compound according to claim 2, an initiator and an organic solvent.

10. A kit comprising a first compartment comprising at least one compound according to claim 2, and an organic solvent, and a second compartment comprising the photoinitiator.

11. A method for manufacturing a substrate coated with a thin, amorphous, emissive, photo-crosslinkable and non-doped small molecule-based film, comprising the following steps:
   a) providing a composition comprising at least one compound of general formula according to claim 2, a solvent and a photoinitiator;
   b) depositing the composition obtained in a) onto a substrate.

12. The photopolymerizable emissive compound of general formula (I) according to claim 1, wherein X and Y each independently represent a phenyl group.

13. The photopolymerizable emissive compound of general formula (I) according to claim 1, wherein A and B each independently represent a —CHMe— group.

14. The photopolymerizable emissive compound of general formula (I) according to claim 1, wherein $L_1$ and $L_2$ each independently represent an alkyl group comprising 3 to 10 carbon atoms, linear or branched, that may be interrupted by one or several atoms —O—, —N— or —S—; said group being optionally substituted with at least one alkyl, alkene, alkyne, oxo, amine, amide, cyano, hydroxyl, carboxy group.

15. The photopolymerizable emissive compound of general formula (I) according to claim 1, wherein $T_1$ and $T_2$ simultaneously represent an acryloyl group or an alkyloxetane group.

16. The photopolymerizable emissive compound of general formula (I) according to claim 1, wherein Z represents an aldehyde, dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

17. The intermediate compound according to claim 3, wherein X and Y each independently represent a phenyl group.

18. The intermediate compound according to claim 3, wherein A and B each independently represent a —CHMe— group.

19. The intermediate compound according to claim 3, wherein Z represents an aldehyde, dicyanovinylidene, cyanovinylidene, benzothiadiazole group or an alkyl ester group comprising at least one photopolymerizable group selected from at least one acryloyl, alkylacryloyl, oxetane, alkyloxetane, styryl, allyl, acrylamide, methacrylamide or cinnamate.

* * * * *